(12) United States Patent
Yu et al.

(10) Patent No.: US 8,343,778 B2
(45) Date of Patent: Jan. 1, 2013

(54) MICROFLUIDIC MICROARRAY ASSEMBLIES AND METHODS OF MANUFACTURING AND USING

(75) Inventors: Hua Zhong Yu, Burnaby (CA);
Meenakshinathan Parameswaren, Coquitlam (CA); Paul Chi Hang Li, Coquitlam (CA); Xing Yue Peng, Burnaby (CA); Hong Chen, Vancouver (CA); Wa Lok Chou, Vancouver (CA)

(73) Assignee: Simon Fraser University, Burnaby, British Columbia (CA)

( * ) Notice: Subject to any disclaimer, the term of this patent is extended or adjusted under 35 U.S.C. 154(b) by 928 days.

(21) Appl. No.: 11/721,423
(22) PCT Filed: Dec. 12, 2005
(86) PCT No.: PCT/CA2005/001884
§ 371 (c)(1),
(2), (4) Date: Oct. 26, 2009
(87) PCT Pub. No.: WO2006/060922
PCT Pub. Date: Jun. 15, 2006

(65) Prior Publication Data
US 2010/0041562 A1 Feb. 18, 2010

Related U.S. Application Data

(60) Provisional application No. 60/634,598, filed on Dec. 10, 2004.

(51) Int. Cl.
*G01N 33/53* (2006.01)
(52) U.S. Cl. .......... 436/809; 436/43; 436/52; 436/53; 436/149; 436/164; 436/165; 436/166; 436/172; 436/174; 436/180; 436/518; 436/524; 436/805; 436/807; 422/52; 422/63; 422/64; 422/82.05; 422/82.08; 422/82.09; 422/82.11; 422/407; 422/425; 422/426; 422/429; 422/500; 422/501; 422/502; 422/503; 422/504; 435/164; 435/165; 435/283.1; 435/286.4; 435/287.1; 435/287.2; 435/288.5; 435/288.7; 435/4; 435/5; 435/6.11; 435/6.12; 435/6.19; 435/7.1; 435/7.2; 435/7.9; 435/29; 204/403.01; 204/450; 356/450; 506/3; 506/7; 506/9; 506/10; 506/32; 506/39

(58) Field of Classification Search ............ 422/102, 422/52, 63, 64, 82.05, 82.08, 82.09, 82.11, 422/99, 407, 425, 426, 429, 500, 501, 502, 422/503, 504; 435/164, 165, 283.1, 286.4, 435/287.1, 287.2, 288.5, 288.7, 4, 5, 6.11, 435/6.12, 6.19, 7.1, 7.2, 7.9, 29; 436/149, 436/164, 165, 166, 172, 174, 180, 518, 524, 436/805, 809, 43, 52, 53, 807; 204/403.01, 204/450; 356/450; 506/3, 7, 9, 10, 32, 39
See application file for complete search history.

(56) References Cited

U.S. PATENT DOCUMENTS
5,413,939 A * 5/1995 Gustafson et al. ............ 436/518
(Continued)

FOREIGN PATENT DOCUMENTS
WO WO0210448 A1 2/2002
(Continued)

OTHER PUBLICATIONS

Kido, "Disc-based immunoassay microarrays", Analytica Chimica Acta 411 (2000) 1-11.*
(Continued)

*Primary Examiner* — Dennis M White
(74) *Attorney, Agent, or Firm* — Chernoff, Vilhauer, McClung & Stenzel, LLP

(57) ABSTRACT

The invention encompasses microfluidic microarray assemblies (MMA) and subassemblies and methods for their manufacture and use. In one embodiment, first and second channel plates are provided and are sealingly connected to a test chip in consecutive steps. Each plate includes microfluidic channels configured in a predetermined reagent distribution pattern. The test chip comprises a plurality of discrete test positions, each test position being located at the intersection between a first predetermined reagent pattern and a second predetermined reagent pattern, wherein at least one of said patterns is non-linear. The first channel plate allows the distribution of a first reagent on said test chip, wherein said first reagent is immobilized at said test positions. The second channel plate allows the distribution of a second reagent on said test chip, wherein said second reagent comprises a plurality of different test samples.

84 Claims, 16 Drawing Sheets

U.S. PATENT DOCUMENTS

| | | | |
|---|---|---|---|
| 5,677,195 | A | 10/1997 | Winkler et al. |
| 6,342,349 | B1 | 1/2002 | Virtanen |
| 6,620,478 | B1 | 9/2003 | Ohman |
| 6,709,869 | B2 | 3/2004 | Mian et al. |
| 2002/0168652 | A1 | 11/2002 | Werner et al. |
| 2003/0059803 | A1* | 3/2003 | Werner et al. .............. 435/6 |
| 2003/0096434 | A1* | 5/2003 | Krutzik .............. 436/524 |
| 2005/0026148 | A1 | 2/2005 | Rexhausen et al. |
| 2005/0083781 | A1 | 4/2005 | Caren et al. |

FOREIGN PATENT DOCUMENTS

| | | |
|---|---|---|
| WO | WO02051537 A1 | 7/2002 |
| WO | 02/095651 A2 | 11/2002 |

OTHER PUBLICATIONS

Lahann et al, "Reactive Polymer Coatings: A First Step toward Surface Engineering of Microfluidic Devices" Anal. Chem. 2003, 75, 2117-2122.*

Peng, X.Y, et al., "Fast DNA Hybridization on a Multi-Sample Multi-probe Microfluidic Microarray Compact Disc", May 2005, 2005 NSTI Nanotechnology Conference and Trade Show—NSTI Nanotech 2005 Technical Proceedings 2005 Nano Science and Technology Institutes US, p. 332-335.

Zoval et al. (Jan. 2004) "Centrifuge-based Fluidic Platforms" Proceedings of the IEEE, 92(1), 140-153.

Duffy et al. (1998) "Rapid Prototyping of Microfluidic Systems in Poly(dimethylsiloxane)" Anal. Chem., 70, 4974-4984.

Campas et al. (2004) "DNA Biochip Arraying, Detection and Amplification Strategies" Trends in Analytical Chemistry, 23(1), 49-62.

Lee et al. (2001) "SPR Imaging Measurements of 1-D and 2-D DNA Microarrays Created from Microfluidic Channels on Gold Thin Films" Anal. Chem., 73(22), 5525-5531.

Hirschberg et al. (2004) "Detection of Phosphorylated Peptides in Proteomic Analyses Using Microfluidic Compact Disk Technology" Anal. Chem., 76(19), 5864-5871.

Situma et al. (2005) "Fabrication of DNA Microarrays Onto Poly(methyl methacrylate) with Ultraviolet Patterning and Microfluidics for the Detection of Low-abundant Point Mutations" Anal. Biochem., 340, 123-135.

Gustafsson et al. (2004) "Integrated Sample Preparation and MALDI Mass Spectrometry on a Microfluidic Compact Disk" Anal. Chem., 76(2), 345-350.

Duffy et al. (1999) "Microfabricated Centrifugal Microfluidic Systems: Characterization and Multiple Enzymatic Assays" Anal. Chem., 71(20), 4669-4678.

Lai et al. (2004) "Design of a Compact Disk-Like Microfluidic Platform of Enzyme-Linked Immunosorbent Assay" Anal. Chem., 76(7), 1832-1837.

Kim et al. (2004) "Large Area Two-Dimensional B Cell Arrays for Sensing and Cell-Sorting Applications" Biomacromolecules, 5(3), 822-827.

Khademhosseini et al. (2004) "A Soft Lithographic Approach to Fabricate Patterned Microfluidic Channels" Anal. Chem., 76(13), 3675-3681.

Chen et al. (1998) "Micropatterned Surfaces for Control of Cell Shape, Position, and Function" Biotechnol. Prog., 14(3), 356-363.

Takano et al. (2002) "Micropatterned Substrates: Approach to Probing Intercellular Communication Pathways" Anal. Chem., 74(18), 4640-4646.

Sternson et al. (2001) "Split-Pool Synthesis of 1,3-Dioxanes Leading to Arrayed Stock Solutions of Single Compounds Sufficient for Multiple Phenotypic and Protein-Binding Assays" J. Am. Chem. Soc., 123(8), 1740-1747.

* cited by examiner

A: amino CGCCGATTGGACAAAACTTAAA
B: amino CGCCAGAGAATACCAAAACTC
A': the complementary sequence of A labelled by Cy5
B': the complementary sequence of B labelled by Cy5

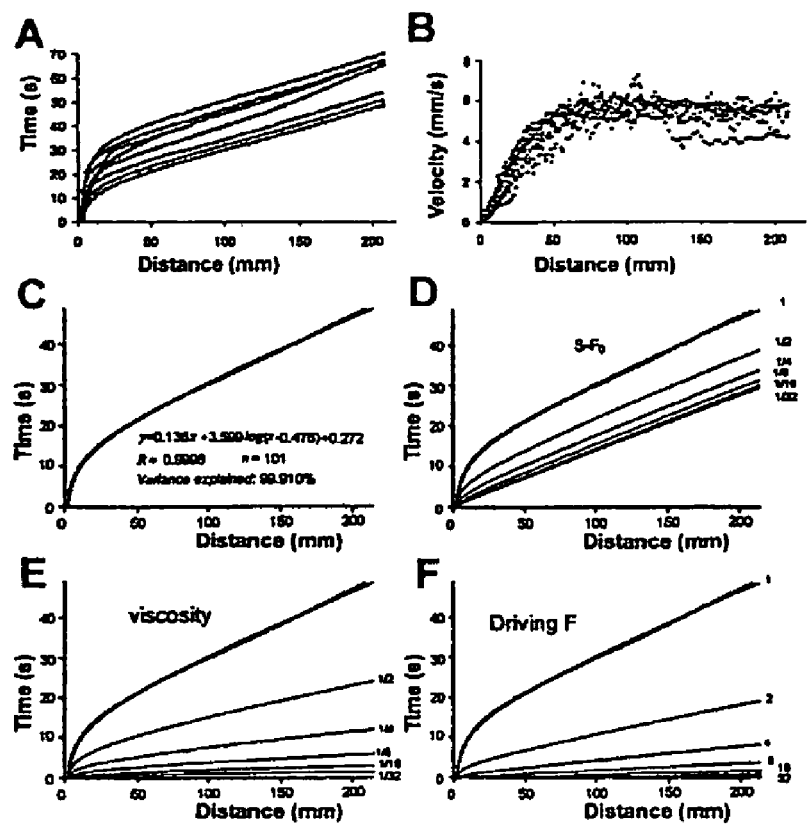
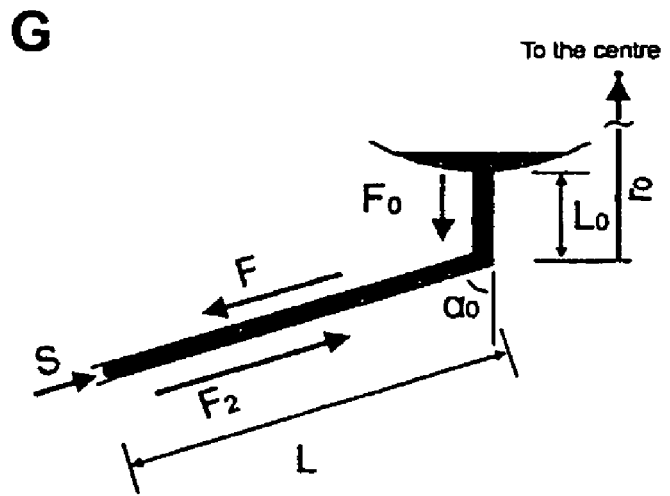
Figure 14

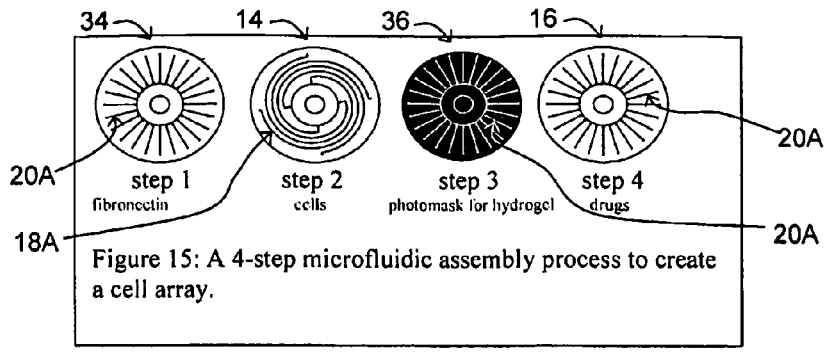

Figure 15: A 4-step microfluidic assembly process to create a cell array.

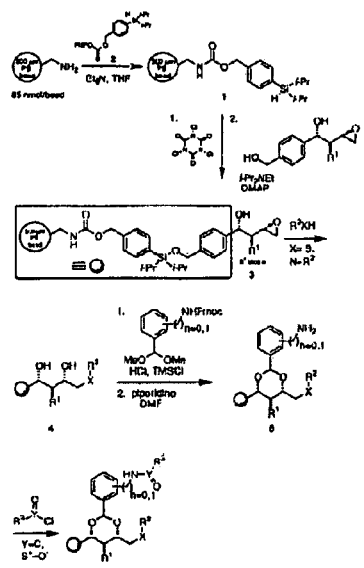

Figure 16: The formation of a linker on a solid surface (1) & a subsequent 3-step reactions for the epoxy alcohol (3) to form various 1,3-dioxanes (6).

*Figure 17: Synthesis of a 1,3-dioxanes library on a MMA*

| Initial stage 1 | Initial stage 2 | Reaction 1 | Reaction 2 | Reaction 3 |
|---|---|---|---|---|
| Radial channel plate sealed with glass chip | | | Spiral channel plate sealed with glass chip | |
| immobilize compound O | Add 3 compounds a | Add 30 compounds b | Add 2 compounds c | Add 10 compounds d |
| O | $Oa_1, Oa_2, Oa_3$ | $Oa_1b_1$—$Oa_1b_{30}$, $Oa_2b_1$—$Oa_2b_{30}$, etc | $Oa_1b_1c_1$—$Oa_1b_{30}c_1$, etc | $Oa_1b_1c_1d_1$—$Oa_1b_{30}c_1d_{10}$, etc |
| total: 1 | total: 3 | total: 30+30+30=90 | total: 2*90=180 | total: 180*10=1800 |
| | 3 groups of 32 lines | three sets of 30 groups | 2 groups of 48 lines | Two sets of 40 groups |

MICROFLUIDIC MICROARRAY ASSEMBLIES AND METHODS OF MANUFACTURING AND USING

RELATED APPLICATION

This application claims the benefit of the filing date of U.S. provisional patent application No. 60/634,598 filed 10 Dec. 2004 which is hereby incorporated by reference.

FIELD OF THE INVENTION

This application relates to the manufacture and use of microarray devices using microfluidic reagent distribution techniques.

BACKGROUND

DNA microarray chips are well known in the prior art. Such microarrays are typically formed either by on-chip photolithographic synthesis of oligonucleotides[1] or by on-chip spotting of synthesized oligonucleotides.[2] Both approaches have significant limitations. The photolithographic synthesis method is expensive, limited to 50-mer oligonucleotide synthesis, and cannot be used for cDNA. The spotting method uses expensive robots and pins, and wastes the oligonucleotide samples unless many microarray slides are prepared during one spotting procedure. In both cases, each microarray slide created can be used with only one sample. Therefore, multiple samples typically require the use of multiple microarray slides. Moreover, microarray slides usually require large volumes of sample (e.g. 200 µL).

In some cases the spotting method has been performed on chips containing microfluidic channels.[3, 4, 5, 6, 7] While spotting oligonucleotides into a microfluidic channel may reduce the required sample volume, the density of the resultant microarray is limited by the space required on the chip required to accommodate complicated liquid handling interfaces, such as microtubes, micropumps electrical contacts and the like. Heretofore high density microarrays have not been successfully achieved using microfluidic techniques. For example, some groups have used a stencil approach to create parallel, linear microfluidic channels on separate chips.[8, 9, 10, 11] The microfluidic channels are then used to generate microarrays at intersecting points between the linear channel patterns. However, this approach has thus far not been employed to generate high density arrays (i.e. greater than about 16×16 channels).[12] This is likely due to the difficulty in reliably flowing reagent fluid through large numbers of microchannels using conventional fluid delivery techniques, such as electrical current or pressure pumping. For example, it is technically difficult and cumbersome to couple miniature electrical connections or pump conduits to large numbers of microchannels without causing fluid leakage or other undesirable chip failures.

Apart from electric and pressure pumping, the use of centrifugal force is known in the prior art in some DNA hybridization applications using pre-spotted microarrays.[13, 14, 15, 16, 17, 18, 19, 20, 21] For example, DNA hybridizations have been achieved on circular discs in which centrifugal force has been used to pump liquids through radial channels in which a microarray is spotted.[22] However, in this example the liquid pumping method is used in the radial direction only and is used only once on the chip. Centrifugal pumping has thus far not been used to form an intersecting pattern of reagents on a microarray chip.

The need has therefore arisen for improved devices and methods for producing microarray devices using microfluidic techniques to enable the efficient testing of multi-probe, multi-sample reagent combinations.

SUMMARY OF INVENTION

In accordance with the invention, a microarray device fabricated using microfluidic reagent distribution techniques is provided. As described herein, the invention encompasses microfluidic microarray assemblies and subassemblies and methods for their manufacture and use.

In one embodiment of the invention, the microarray device comprises a test chip having a plurality of discrete, spatially predetermined test positions, each of the test positions being located at the intersection between a first predetermined reagent pattern and a second predetermined reagent pattern. In one embodiment at least one of the first and second predetermined reagent patterns is non-linear. For example at least one of the predetermined patterns may be a spiral pattern. In one particular embodiment, one of the predetermined reagent patterns is a radial pattern and another of the predetermined reagent patterns is a spiral pattern. In another particular embodiment, both of the predetermined reagent patterns are spiral patterns.

The microarray device also comprises channel plates having microfluidic channels configured for distributing reagents on the test chip in the predetermined reagent patterns when the channel plates are sealingly connected to the test chip. For example, a first channel plate may be provided having a plurality of first microfluidic channels for distributing at least one first, reagent on the test chip in the first predetermined reagent pattern. Similarly, a second channel plate may also be provided having a plurality of second microfluidic channels for distributing at least one second reagent on the test chip in the second predetermined reagent pattern. In use, the first and second channel plates may be connected to the test chip separately and consecutively. For example, in one embodiment the first channel plate is connected to the test chip and the at least one first reagent is distributed on the test chip through the first microfluidic channels in the first predetermined reagent pattern. The first reagent is then immobilized on the test chip. Next, the first channel plate is removed, the second channel plate is connected to the test chip and the at least one second reagent is distributed on the test chip through the second microfluidic channels in the second predetermined reagent pattern.

In one embodiment, the at least one first reagent may comprise a plurality of separate probes each distributed to selected test position(s) of the microarray in the first predetermined reagent pattern and the at least one second reagent may comprise a plurality of test samples each distributed to selected test position(s) of the microarray in the second predetermined reagent pattern. Positive or negative reactions between the probes (or other first reagent) and test samples (or other second reagent) may then be detected at the microarray test positions. For example, hybridization between selected nucleic acid probes and selected nucleic acid samples may be detected at particular test positions. In addition to nucleic acids and oligonucleotides, the first and second reagents may be selected from the group consisting of proteins, peptides, peptide-nucleic acids, oligosaccharides, antigens, immunoglobulins, cells, organelles, cell fragments, small molecules and chimeric molecules.

Various means may be provided for causing the first and second reagents to flow through the respective first and second microfluidic channels. In one particular embodiment, the test chip and the first and second channel plates are centrosymmetrical, for example circular. Subassemblies comprising the chip and one or more plates may be conveniently loaded into a spinning apparatus to generate centrifugal forces sufficient to cause fluid flow through the microfluidic channels.

BRIEF DESCRIPTION OF DRAWINGS

In drawings which illustrate various embodiments of the invention but which are not intended to be construed in a limiting manner:

FIG. 3A is a schematic view of a blank test chip.

FIG. 3(B2) is a schematic view of a second channel plate having a plurality of second microfluidic channels configured in a left spiral pattern.

FIG. 3C is a schematic view showing the intersecting reagent distribution patterns on the test chip.

FIG. 3D is a schematic view showing positive test results at microarray test positions located at the intersections between the reagent distribution patterns of FIG. 3C.

FIG. 14 is a series of graphs showing theoretical model and sensitivity tests of centrifugal pumping in the spiral microfluidic channels. (A) The transit times of the flow in 96 spiral microfluidic channels were plotted against distance. (B) The velocities of the flow as calculated from the slopes of all 96 traces in (A). (C) Curve fitting of the experimental data in one trace (circles) to the theoretical model (line), resulting in R=0.9995. (D) Sensitivity test of S–$F_0$ ($\frac{1}{2}$, $\frac{1}{4}$, $\frac{1}{8}$, $\frac{1}{16}$ and $\frac{1}{32}$ of the original value). (E) Sensitivity test of viscosity ($\frac{1}{2}$, $\frac{1}{4}$, $\frac{1}{8}$, $\frac{1}{16}$ and $\frac{1}{32}$ of the original value). (F) Sensitivity test of F (2, 4, 8, 16, 32 time of the original value). (G). Schematic diagram of a single spiral microfluidic channel near the inlet reservoir.

FIG. 15 is a schematic view of a method for conducting cellomics studies using a microarray device in accordance with the invention.

FIG. 16 is a reaction scheme, for forming various 1,3 dioxanes.

FIG. 17 is a table showing the step-wise-synthesis of a 1,3 dioxane library on a microarray device.

DETAILED DESCRIPTION OF THE INVENTION

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive, sense.

With reference to the enclosed drawings, this invention relates to microarray devices fabricated using microfluidic reagent distribution techniques. The invention encompasses microfluidic microarray assemblies and subassemblies and methods for their manufacture and use.

Figure 1:
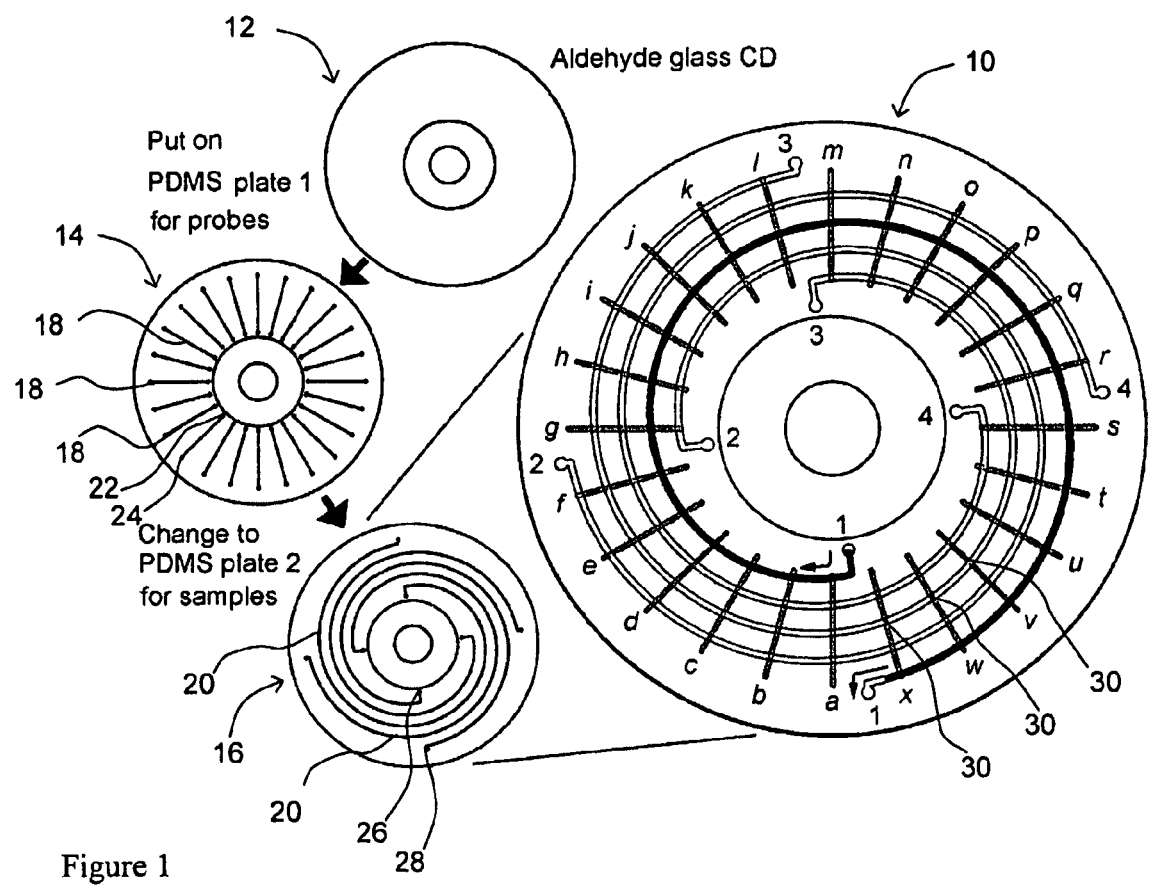
FIG. 1 is a schematic view showing the assembly steps for fabricating a microarray device by combining a test chip and first and second channel plates.
Figure 2:
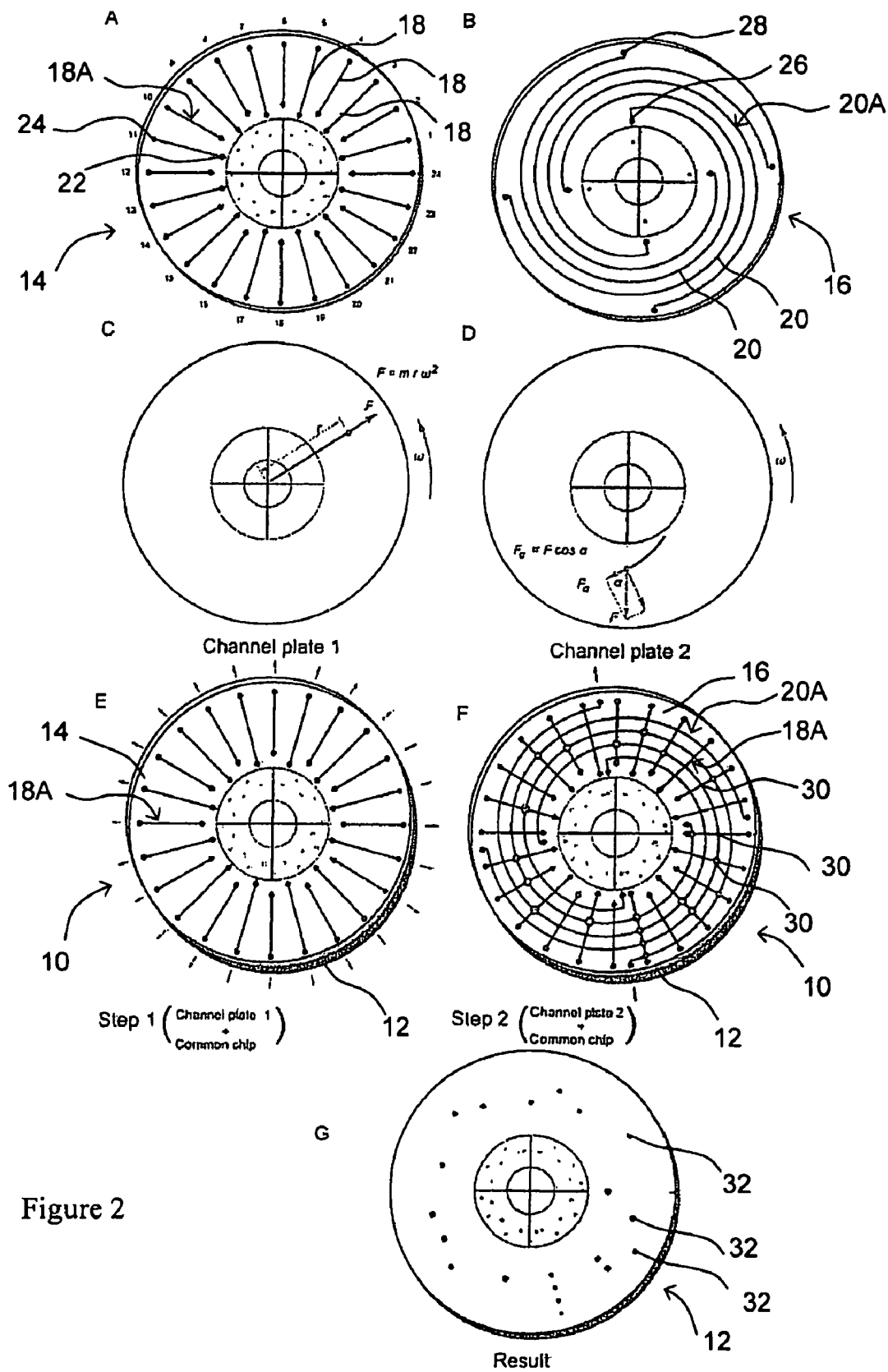
FIG. 2A is a schematic view of a first channel plate having a plurality of first microfluidic channels configured in a radial pattern.
FIG. 2B is a schematic view of second channel plate having a plurality of second microfluidic channels configured in a spiral pattern.
FIG. 2C is a schematic view showing a first dimensional, centrifugal force (F) used to distribute liquids in the radially configured first microfluidic channels of FIG. 2A.
FIG. 2D is a schematic view showing a second dimensional centrifugal force (F cos α) used to distribute liquids in the spiral second microfluidic channels of FIG. 2B.
FIG. 2E is a schematic view showing the first channel plate sealingly connected to a test chip.
FIG. 2F is a schematic view, showing the second channel plate sealingly connected to the test chip after removal of the first channel plate.
FIG. 2G is a schematic view of a test chip showing positive test results at select microarray test positions after removal of the second channel plate.

The general concept of a first embodiment of the invention is shown in FIGS. 1 and 2. In this embodiment a microfluidic microarray assembly (MMA) 10 is illustrated which is produced by the combination of a test chip (of "common chip") 12 and a first channel plate 14 and/or a second channel plate 16. As described in detail below, channel plates 14, 16 may be each separately connected to test chip 12 in consecutive order, to deliver reagents to test chip 12 (such as probes or test samples) in predetermined patterns defined by microfluidic charmer patterns. That is, in one example, first channel plate 14 is first sealingly connected to test chip 12 to deliver a plurality of probes thereto. First channel plate 14 is then removed from test chip 12 and second channel plate 16 is sealingly connected to test chip 12 to deliver a plurality of samples thereto. The invention thus enables the efficient formation of high density multi-probe, multi-sample microarrays by employing microfluidics.

As shown best in FIGS. 1 and 2, first channel plate 14 has a plurality of first microfluidic channels (or "microchannels") 18 arranged in a first predetermined reagent pattern 18A, such as a radial pattern comprising a plurality of linear, radially extending segments. In the example of FIGS. 1 and 2, first channel plate 14 has 24 separate radially extending microfluidic channels 18. Similarly, second channel plate 16 has a plurality of second microfluidic channels 20 arranged in a second predetermined reagent pattern 20A, such as a spiral pattern. In the example of FIGS. 1 and 2, second channel plate 16 shown in FIGS. 1 and 2 has 4 separate spiral microfluidic channels 20.

Reservoirs are located at each end of microfluidic channels 18, 20 in fluid communication therewith. More particularly, each first microfluidic channel 18 has an inlet reservoir 22 at one end thereof and an outlet reservoir 24 at the other end thereof and each second microfluidic channel 20 has an inlet reservoir 26 at one end thereof and an outlet reservoir 28 at the other end thereof (FIGS. 2A and 2B). In the case of high density microarrays, the inlet and/pr outlet reservoirs may be staggered in rows to fit within the available space on MMA 10 (FIGS. 4 and 6-9).

As explained in detail below, first and second predetermined reagent patterns 18A, 20A, and hence the geometric configurations of first and second microfluidic channels 18, 20, preferably differ. For example, first predetermined reagent pattern 18A may be a radial pattern and second predetermined reagent pattern 20A may be a spiral pattern, or vice versa. This results in an intersecting pattern of reagent deposition on test chip 12 when each of the channel plates 14, 16 is consecutively sealed to test chip 12 and reagents are flowed through microfluidic channels 18, 20 as described below.

For example, in FIGS. 1 and 2E, when first channel plate 14 is sealed with test chip 12, one or more first reagents can be loaded into inlet reservoirs 22 and flowed through first microfluidic channels 18 to outlet reservoirs 24. This results in the distribution of the first reagent in a radial pattern 18A on test chip 12. As described below, the first reagent is then immobilized on test chip 12 and first channel plate 14 is removed. Second channel plate 16 is then sealed to test chip 12 (FIGS. 1 and 2F). One or more second reagents are loaded into inlet reservoirs 26 and flowed through second microfluidic channels 20 to outlet reservoirs 28. This results in the distribution of the second reagent in a spiral pattern 20A on test chip 12. The intersection points between first and second predetermined patterns 18A, 20A (in this case the radial pattern and the spiral pattern) defines a plurality of microarray test positions 30 on test chip 12. If the first reagent reacts with the second reagent at select test positions 32, a positive test result is obtained (FIG. 2G). For example, as discussed further below, a positive test result could indicate reaction (e.g. hybridization) between the first reagent and the second reagent, formation of a reaction product, modification of a biochemical or cellular parameter or the like.

The number of microarray test positions 30 which are created from the intersection points of first and second predetermined reagent patterns 18A, 20A on test chip 12 depends upon the number and configuration of microfluidic channels 18, 20 on first and second channel plates 14, 16, respectively. For example, in this embodiment of the invention, each line of the first reagent pattern produced by first microfluidic channels 18 intersects only once with each line of the second reagent pattern produced by second microfluidic channels 20. Thus, if first channel plate 14 has x microfluidic channels 18 and second channel plate 16 has y microfluidic channels 20, the resulting microarray has x*y number of intersection points or test positions 30. In FIGS. 1 and 2, first channel plate 14 has x=24 radial microfluidic channels 18 and second channel plate 16 has y=4 spiral microfluidic channels 20. The resulting microarray has 24*4=96 test positions 30 on test chip 12. Preferably, there is only one intersection point between each line of the first reagent pattern produced by first microfluidic channels 18 and each line of the second reagent pattern produced by second microfluidic channels 20. However, it is possible to design first and second channel plates 14, 16 with first and second predetermined reagent patterns 18A, 20A having more than one intersection, point between each set of lines. Further, the first and second reagent distribution patterns formed on test chip 12 may in some cases comprise a plurality of discrete reagent spots rather than a continuous line or lines of reagent.

Figure 3:
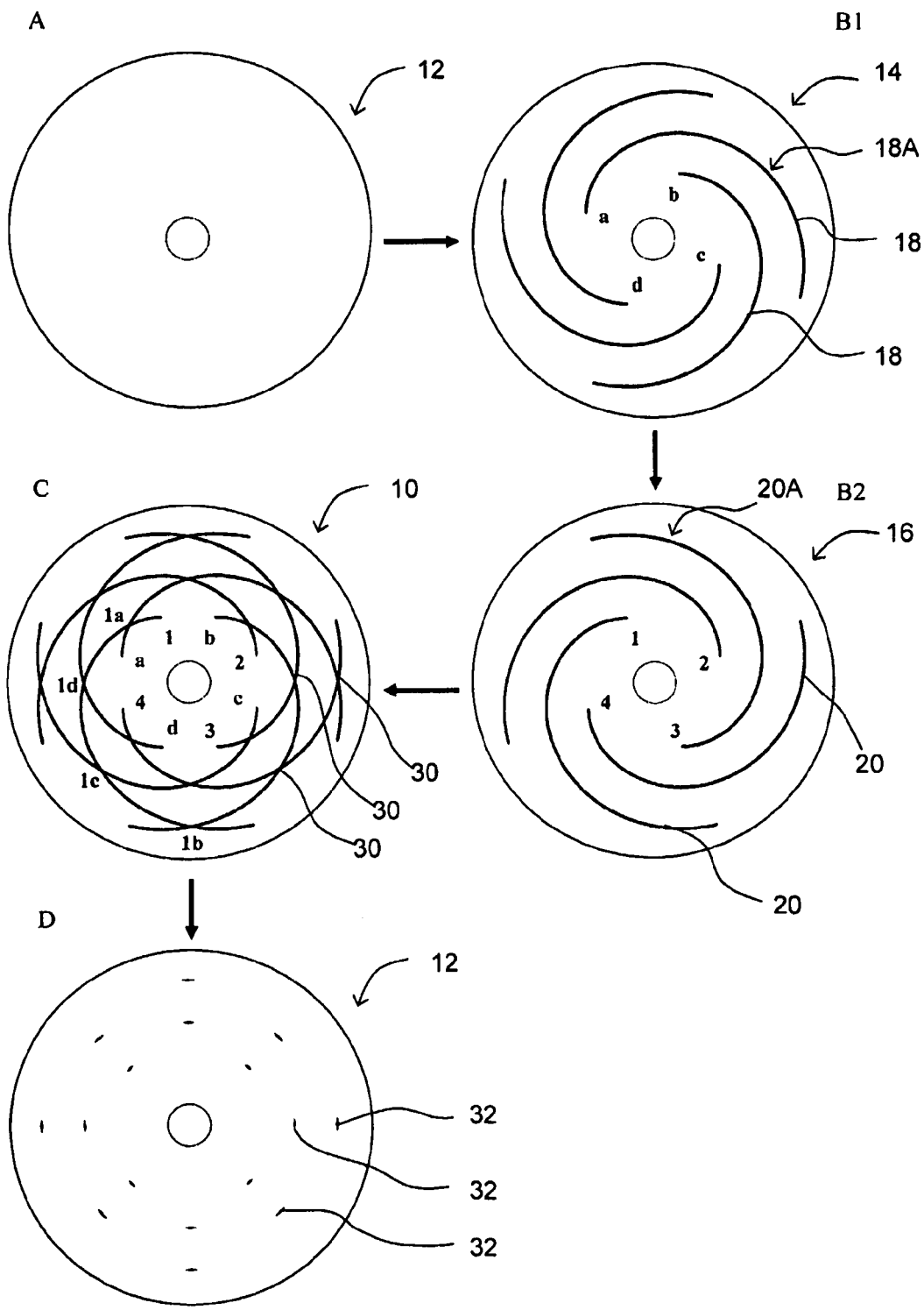
FIG. 3(B1) is a schematic view of a first channel plate having a plurality of first microfluidic channels configured in a right spiral pattern.

FIG. 3 shows another example of the general concept of the invention. In this embodiment both first and second channel plates 14, 16 produce non-linear reagent distribution patterns on test chip 12. In this embodiment, the first predetermined reagent pattern 18A may be a right spiral pattern and the second predetermined reagent pattern 20A may be a left spiral pattern, or vice versa. FIG. 3A shows test chip 12 having no reagents distributed thereon. Test chip 12 is sealed with first channel plate 14 having four microfluidic channels 18 (*a-d*) arranged in a right spiral pattern 18A. One or more first reagents can be loaded into and flowed through first microfluidic channels 18. This results in the distribution of the first reagent in a right spiral pattern 18A on test chip 12. As described below, the first reagent is then immobilized on test chip 12 and first channel plate 14 is removed. Second channel plate 16 having four microfluidic channels 20 (1-4) arranged in a left spiral pattern 20A is sealed with test chip 12. One or more second reagents is loaded into and flowed through second microfluidic channels 20 and results in the distribution of the second reagent in a left spiral pattern 20A oh test chip 12. The intersection points between first and second reagent patterns 18A, 20A define a microarray of test positions 30 (e.g. 1*a*, 1*b*, 1*c*, 1*d*, etc.—FIG. 3C). Positive test results between first and second reagents may occur at select test positions 32 (FIG. 3D). In FIG. 3, first channel plate 14 has x=4 right spiral microfluidic channels 18 and second channel plate 16 has y=4 left spiral microfluidic channels 20. The resulting microarray has 4*4=16 test positions 30 on test chip 12.

It will be appreciated by a person skilled in the art that alignment between first predetermined reagent pattern 18A and second predetermined reagent pattern 20A on test chip 12 is not critical, and an intersecting angle of exactly 90 degrees is not required. Persons skilled in the art will also appreciate that the arrangement of first and second microfluidic channels 18, 20 in first and second channel plates 14, 16 are interchangeable. In other words, first channel plate 14 may have first microfluidic channels 18 arranged in a spiral pattern and second channel plate 16 may have second microfluidic channels 20 arranged in a radial pattern (FIGS. 1 and 2). Similarly, first channel plate 14 may have first microfluidic channels 18 arranged in a left spiral pattern and second channel plate 16 may have second microfluidic channels 20 arranged in a right spiral pattern (FIG. 3).

It will also be appreciated by a person skilled in the art that many variations in the configuration of first and second predetermined reagent patterns 18A, 20A are possible. For example, the spiral pattern of second channel plate 16 of FIGS. 1 and 2 comprise 360° or "full spirals". In other examples other spiral configurations or other curved patterns could be employed. For example, the left and right spiral patterns of FIG. 3 are 180° or "half spirals". This ensures that each left spiral segment will intersect with each right spiral segment only once (to form one test position 30). Further, as explained below, the spiral geometries may be selected to confer equiforce characteristics, thereby ensuring that liquid flows through each of the microfluidic channel segments at approximately equal flow rates when centrifugal force is applied. Other spiral geometries or other non-linear patterns may also be employed, such as equiangular spirals.

Test chip 12 may be made of a variety of materials, for example glass. Test chip 12 may also be coated with different compounds, for example, a glass chip may be aldehyde-functionalized. Channel plates 14, 16 may be made of a polymeric material, for example polydimethylsiloxane (PDMS).

Figure 4:
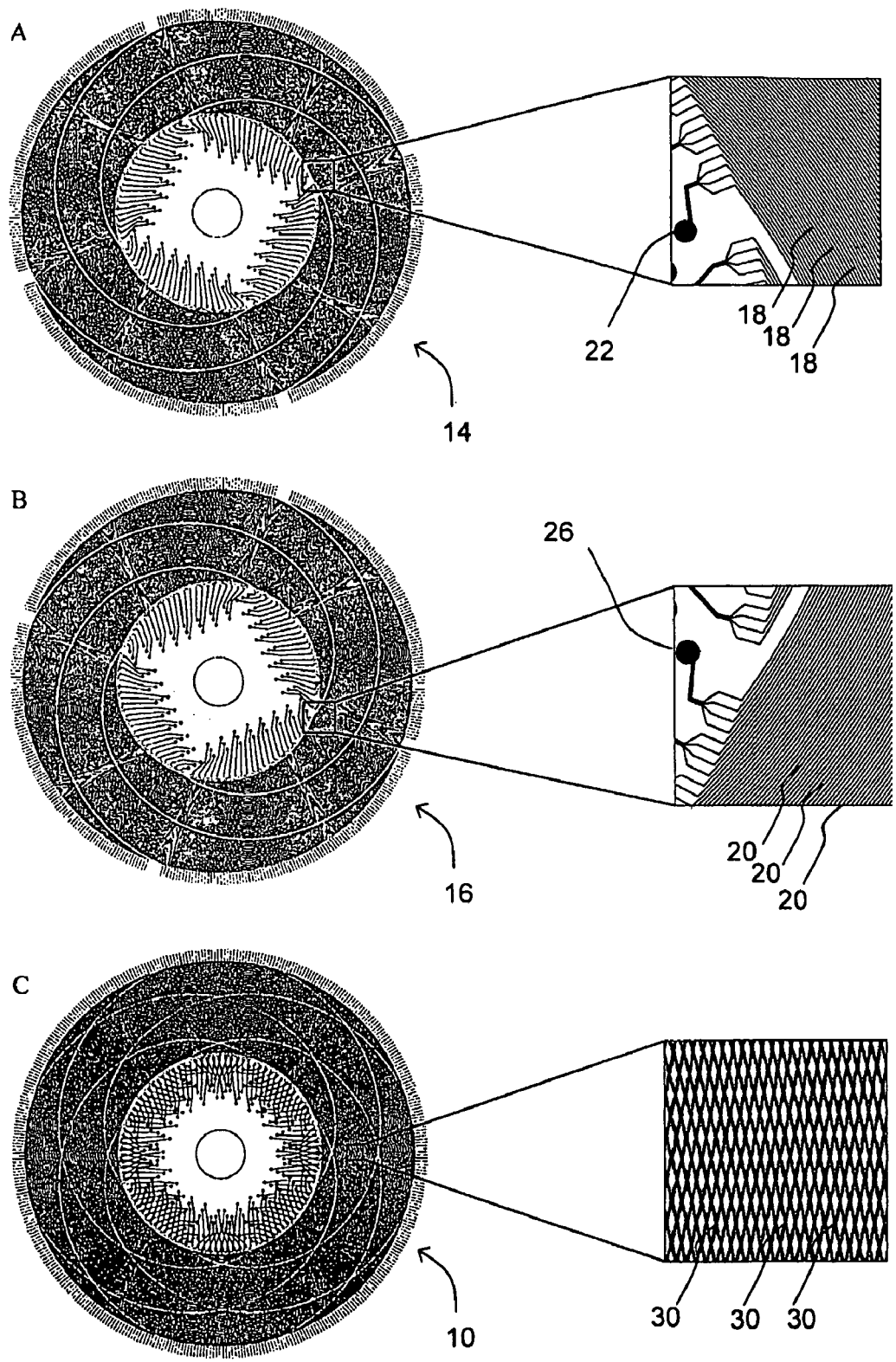
FIG. 4A is a plan view of a first channel plate having a plurality of closely spaced first microfluidic channels configured in a right spiral pattern. The inset shows selected channels in fluid communication with fluid inlet reservoirs.
FIG. 4B is a plan view of a second channel plate having a plurality of closely spaced second microfluidic channels configured in a left spiral pattern. The inset shows selected channels in fluid communication with fluid inlet reservoirs.
FIG. 4C is a plan view showing the intersecting reagent distribution patterns applied to a test chip. The inset shows selected test positions formed by the intersections of the first and second reagent distribution patterns.

FIG. 4 shows diagrams of first and second channel plates 14, 16 having 96 high density microfluidic channels. FIG. 4A shows a first channel plate 14 having 96 microfluidic channels 18 arranged in a right spiral pattern. The inset shows inlet reservoir 22 for loading a first reagent thereinto. FIG. 4B shows second channel plate 16 having 96 microfluidic channels 20 arranged in a left spiral pattern. The inset shows inlet reservoir 26 for loading a second reagent thereinto. FIG. 4C shows the intersection points of the two spiral patterns of first and second channel plates 14, 16. The intersection points define a dense microarray of 9216 (96×96) test positions 30.

In alternative embodiments of the invention, the MMA 10 may be formed from the assembly of one or more additional channel plates. Such additional channel plates may comprise microfluidic channels arranged in a similar pattern to either first or second channel plates 14, 16, or the microfluidic channels may be arranged in other patterns, and may be used to deliver additional reagents, reagent primers or other reagent modifiers, detectors or other materials to test positions 30 on test chip 12.

In another embodiment of the invention, first and second channel plates 14, 16 may be sealed to each other and used with or without test chip 12. In this embodiment, first and second channel plates 14, 16 may include some means for preventing first microfluidic channels 18 from being in fluid communication with second microfluidic channels 20 when respective first and second reagents are flowed therethrough. For example, assembled plates 14, 16 could contain membrane valves. In another example, regulated fluid flow through channels 18, 20 could be achieved by spinning the plates at different speeds to achieve selective fluid flow through channels having different geometric patterns (e.g. radial (linear) channels versus spiral (curved) channels).

For commercial production, immobilization of one or more first reagents could be done in a factory and users could purchase a pre-fabricated test chip 12 with one or more first reagents pre-affixed to test chip 12 in first predetermined pattern 18A. For example, the first reagents could consist of a plurality of different probes arranged in an array corresponding to pattern 18A. Such a pre-fabricated test chip 12 could be used with one, or more channel plates 16 for applying one or more second reagents to test chip 12 in a second predetermined reagent pattern 20A. Any reactions between the first reagents and the second reagents at test locations 30 could be determined by the user. Alternatively, users could purchase a kit comprising test chip 12 and two or more channel plates 14, 16; in this case users could perform both the steps of distributing and immobilizing the first reagent on test chip 12 as well as testing of reactions between the first and second reagents on test chip 12 (e.g. between probes and test samples).

As explained above, the invention encompasses methods for both fabricating and using microarray devices, such as MMA 10. Various means may be used to induce and regulate the flow of reagent(s) deposited on chip 12 for the purpose of microarray formation and testing. In use, after first channel plate 14 is sealed with test chip 12, one or more first reagents are loaded into inlet reservoirs 22 of first microfluidic channels 18. To initiate the flow of and to distribute the first reagents in first microfluidic channels 18, a force is applied to MMA 10 (FIG. 2E). As explained further below, various types of forces may be applied to MMA 10 to induce fluid flow, such as centrifugal force applied by spinning MMA 10. The first reagents are then immobilized or fixed on test chip 12. Immobilization of the first reagent may be achieved by various techniques which are known to persons, skilled in the art. For example, immobilization can be achieved by chemical, mechanical, or biochemical methods such as covalent binding, adsorption, cellular adhesion, protein-protein interactions, polymer encapsulation and so forth. As described further below, one example of chemical immobilization is Schiff-base linkage formed between amine and aldehyde groups on test chip 12.

If necessary, a priming reagent for priming the first reagents may be similarly loaded into and distributed through first microfluidic channels 18 by applying a force to MMA 10.

Other reagents for modifying or labeling the first reagents in some manner could also be used in alternative embodiments of the invention.

After the first reagent is distributed and immobilized on test chip 12 as described above, first channel plate 14 is then removed. In the next step, second channel plate 16 is sealed with test chip 12. One or more second reagents are loaded into inlet reservoirs 26 of second microfluidic channels 20. A force is applied to MMA 10 (FIG. 2F) to cause the second reagents to flow and become distributed through second microfluidic channels 20. If necessary, a priming reagent or other reagent for modifying or labeling the second reagents may also be applied through second microfluidic channels 20. At test positions 30, the first reagents are exposed to the second reagents. If the first and second reagents are capable of reacting with one another, this results in a positive test reaction at select test positions 32.

In a further step, the positive test reactions between the first and second reagents are detected using methods which are well known in the art. For example, fluorescence labeling, biotin labeling, reflectance measurements, and so forth can be used. In addition, novel detection methods such as surface plasmon resonance may also be used.

Once reagents are loaded into one or more inlet reservoirs 22, 26, various means may be used to induce fluid flow through microfluidic channels 18, 20, including the application of centrifugal, electrokinetic or hydrodynamic forces. The application of centrifugal force, sometimes referred to as "centrifugal pumping", provides particular advantages. Centrifugal force may be simply applied by spinning MMA 10 in a disc spinner and avoids the need for complicated fluid handling interfaces. As shown in FIG. 2, distribution of reagents by application of centrifugal force is possible for microfluidic channels 18, 20 arranged in either a radial pattern or a spiral pattern. More particularly, when first channel plate 14 having first microfluidic channels 18 arranged in a radial pattern 18A is sealed against test chip 12, direct centrifugal force (F) is used to distribute the first reagent through microfluidic channels 18 by loading MMA 10 in a spinning device and spinning MMA 10 (FIGS. 2C and 2E). When second channel plate 16 having second microfluidic channels 20 arranged in a spiral pattern 20A is sealed against test chip 12 and the resulting MMA 10 is spun in a spinning device, a component of centrifugal force (F cos α) is used to distribute the second reagent through second microfluidic channels 20 (FIGS. 2D and 2F).

When centrifugal force is used, reagents are loaded into inlet reservoirs 22, 26 at locations near the centre of channel plates 14, 16 respectively. To ensure that all the liquids in inlet reservoirs 22, 26 are distributed into first and second microfluidic channels 18, 20 without spillage, and are retained in outlet reservoirs 24, 28 while spinning the chip, inlet and outlet reservoirs 22, 26, 24, 28 may be disposed at an oblique angle (for example, <90° relative to the central axis of the channel plate). In different embodiments, the reservoirs can carry between 0.1 microlitres and 100 microlitres of reagent depending on the size of channel plates 14, 16 and microfluidic channels 18, 20 formed therein. In one embodiment, the microfluidic channels 18, 20 may be on the order of approximately 60 μm wide and approximately 20 μm deep, although many variations are possible. When MMA 10 is spun, the fluid in the inlet reservoirs 22, 26 is driven into first or second microfluidic channels 18, 20. The fluid then moves outwardly along first or second microfluidic channels 18, 20 until it reaches corresponding outlet reservoirs 24, 28 near the periphery of MMA 10, thereby distributing the reagents along the length of microfluidic channels 18, 20.

The flow speeds of the reagents in first or second microfluidic channels 18, 20 can be controlled by adjusting the rotation speed of MMA 10. For example, the flow speeds can be between 200 rpm and 10,000 rpm. Thus, the residence time or the reaction time of reagents can be controlled, i.e. the time can be adjusted to be long enough to allow for reactions, but short enough to save analysis time.

As discussed above, first and/or second microfluidic channels 18, 20 may be arranged in a spiral shape in one embodiment of the invention. It will be appreciated by persons skilled in the art that any type of spiral shape may be used. However, to achieve uniform and quantitative hybridization (or other types of reactions), it is desirable to ensure an approximately constant flow velocity of liquid reagents in the spiral microfluidic channels 18, 20. If the sample volume of the reagents is many times larger than the channel volume, this constant velocity design for spiral microfluidic channels may not be necessary because there is continuous liquid flow in the microfluidic channels. However, when a small volume of reagent is used (e.g. 1 μL), an approximately constant flow velocity of liquid reagents is desirable.

As described below, the inventors use equiforce spiral patterns in some embodiments of the invention to optimize reagent flow characteristics. The use of spiral microfluidic channels 18, 20 has other advantages. For example, spiral patterns, allow for more efficient use of space on MMA 10 to achieve enhanced microarray densities. In the embodiment of the invention where two spiral patterns are used, this also provides for a symmetrical microarray test position pattern.

As will be apparent to a person skilled in the art, when a circular disc is spun, the centrifugal force increases from the centre of the disc towards the periphery of the disc. Thus, as the centrifugal force increases, the linear speed of fluid in the spiral channels also increases. Thus, to overcome this increase in speed and to achieve an approximately constant linear speed, a special equiforce spiral shape has been designed to be used with this invention. The principle of the equiforce spiral design is described as follows.

Figure 5:
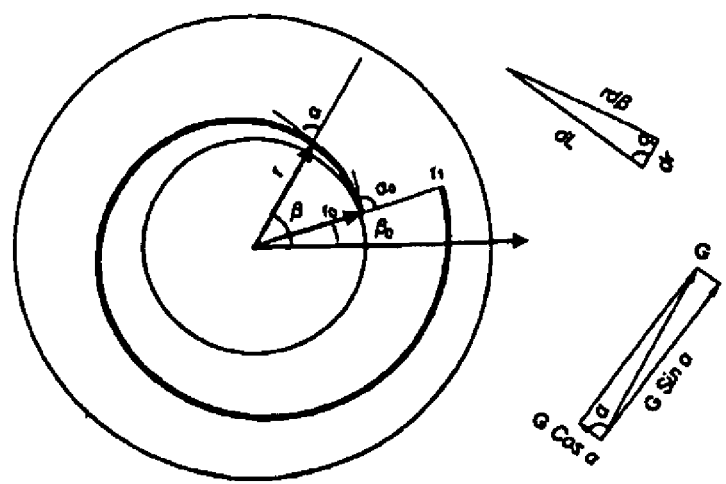
FIG. 5 is a schematic diagram showing the components of centrifugal force (G) acting on a spiral microfluidic channel. An equiforce spiral channel is depicted with the polar coordinates of r and β. The spiral curve starts at $r_0$ and $β_0$ at an angle of $β_0$ that the spiral curve makes with the radius. The spiral curve ends at $r_1$. The top right inset shows an infinitesimal section of the curve showing the angular relation between $rdβ$ and $dr$.

Referring to FIG. 5, the strategy in the design of the equiforce spiral curve is to increase the angle α, or reduce cos α, to compensate for the increasing force G. In the case of a spinning circular disc, G is given by $\omega^2 r$, and the along-channel acceleration ($a_\alpha$) is given by $$a_\alpha = \omega^2 r \cos \alpha \tag{A1}$$

where ω is the angular velocity, r is the radius, and α is the angle that the spiral curve makes with the radius.

At the initial position of the spiral channel, $r = r_0$ and $\alpha = \alpha_0$, thus:

$$a_{\alpha_0} = \omega^2 r_0 \cos \alpha_0 \tag{A2}$$

To maintain a constant along-channel force and acceleration over, the entire spiral channel:

$$a_{\alpha_0} = a_\alpha$$

$$\text{or } r_0 \cos \alpha_0 = r \cos \alpha \tag{A3}$$

Thus, the following equation describes an infinitesimal segment of the equiforce spiral curve (depicted in the inset of FIG. 5), $$\frac{rd\beta}{dr} = \tan\alpha = \frac{\sqrt{1-\cos^2\alpha}}{\cos\alpha} \tag{A4}$$

Substituting k in equation A1 for $$\frac{a_\alpha}{\omega^2}$$

gives:

$$k = \frac{a_\alpha}{\omega^2} = r\cos\alpha \quad (A5)$$

Then from equation A3 gives:

$$\frac{a_{\alpha_0}}{\omega^2} = r_0\cos\alpha_0 = k \quad (A6)$$

Combining equations A4 and A5 gives:

$$\frac{rd\beta}{dr} = \frac{\sqrt{1 - \frac{k^2}{r^2}}}{\frac{k}{r}} \quad (A7)$$

Next, separating the variables, and integrating with the limits of $\beta$ from $\beta_0$ to $\beta$, and r from $r_0$ to r as follows provides:

$$\int_{\beta_0}^{\beta} d\beta = \int_0^r \frac{\sqrt{\frac{r^2}{k^2} - 1}}{r} dr \quad (A8)$$

After integration:

$$\beta - \beta_0 = \sqrt{\left(\frac{r}{k}\right)^2 - 1} - \text{ArcTan}\sqrt{\left(\frac{r}{k}\right)^2 - 1} - \sqrt{\left(\frac{r_0}{k}\right)^2 - 1} + \text{ArcTan}\sqrt{\left(\frac{r_0}{k}\right)^2 - 1} \quad (A9)$$

Finally, after using equations A5 and A6 to replace k, a function is obtained that describes the equiforce spiral curve based on the polar coordinates r and $\beta$:

$$\beta - \beta_0 = \sqrt{\left(\frac{r}{r_0\cos\alpha_0}\right)^2 - 1} - \text{ArcTan}\sqrt{\left(\frac{r}{r_0\cos\alpha_0}\right)^2 - 1} - \text{Tan}\alpha_0 + \alpha_0 \quad (A10)$$

The value of $\alpha_0$ in equation A10 is computed by numerical iteration (Newton's methods). The value of $r_0$ is known; $\beta = \beta_0 + 2\pi$ and $r = r_1$ is used. To assist in the numerical iteration to compute $\alpha_0$, the following partial differential equation is obtained from equation A10 by differentiating it with respect to $\alpha_0$:

$$\frac{\partial(\beta - \beta_0)}{\partial \alpha_0} = 1 - \text{Sec}^2\alpha_0 - \frac{\text{Tan}\alpha_0 - \left(\frac{r}{r_0}\right)^2 \text{Sec}^2\alpha_0 \text{Tan}\alpha_0}{\sqrt{\left(\frac{r}{r_0}\right)^2 \text{Sec}^2\alpha_0 - 1}} \quad (A6)$$

With a computed $\alpha_0$, the equiforce spiral curve can be plotted using equation A10. To obtain the r value at each value of $\beta$ for graph plotting, numerical iteration to compute r was used. To assist in this operation, another partial differential equation obtained from equation A10 by differentiating it with respect to r was used:

$$\frac{\partial(\beta - \beta_0)}{\partial r} = \sqrt{\frac{1}{r_0^2\cos^2\alpha_0} - \frac{1}{r^2}} \quad (A11)$$

In order to calculate the length of liquid column, L, in the spiral microchannel, the following equation was used:

$$L = \frac{1}{2r_0\cos\alpha_0}(r^2 - r_0^2) \quad (A12)$$

In this design, $\alpha_0$ was computed to be 1.4517 radians. With $r_0=24$ mm and $r_1=42$ mm, L was computed to be 208 mm.

In general, in order to achieve a reasonable liquid, flow speed in the spiral microfluidic channels, a higher rotation speed than that for radial microfluidic channels is needed. Based on equation A10, the equiforce spiral microfluidic channel on MMA 10 has a constant component centrifugal acceleration and force. This will be balanced by the liquid viscous force to attain a constant flow speed along the whole equiforce spiral microfluidic channel, regardless of the locations near the centre periphery of MMA 10.

To allow balancing of MMA 10 while it is being spun, the channel plates and test chips can be constructed in a centrosymmetrical geometrical shape (e.g. square, hexagon, octagon, circle, and so on).

Although the use of centrifugal force is desirable, it will be appreciated by a person skilled in the art that liquid reagent flow in MMA 10 can also be initiated by other means. For instance, both hydrodynamic force (using a pump or suction vacuum) and electrokinetic force (using electric voltages) can be used to drive reagents from the inlet reservoir to the outlet reservoir of a microfluidic channel. In these cases, liquid flow does not necessarily need to be directed from the centre to the periphery of MMA 10. For example, if the inlet reservoirs are at the periphery and the outlet reservoirs are at the centre, a single common outlet reservoir located near the centre of MMA 10 could be used for all of the microfluidic channels to save space. In addition, depending on the type of force that is used, an oscillating flow, where the reagent is flowed back and forth between the inlet and outlet reservoirs, can be carried out in the microfluidic channels to enhance sample utilization and detection sensitivity.

As will be appreciated by a person skilled in the art, microarray devices such as MMA 10 having many possible applications, including, but are not limited to, high throughput screening applications, high throughput diagnostic applications, clinical screening applications, clinical diagnostic applications, industrial screening applications, industrial diagnostic applications, genomic applications including research on human genes, pharmacogenomics, proteomics, and many other screening or diagnostic applications. Many different types of reagents or reagent combinations could be used for testing purposes.

More specifically, MMA 10 may be used to perform surface-based reactions such as nucleic acid hybridizations, protein-protein interactions, protein-DNA interactions, protein-peptide nucleic acid (PNA) interactions, cell-drug interactions, oligosaccharide-protein interactions, ligand-receptor interactions and so on. MMA 10 can also be used for small molecule arrays and two-dimensional or multi-dimensional chemical separations as described herein.

The reagents which may be used in association with MMA 10 may be selected from the group consisting of: nucleic acids, oligonucleotides, proteins, peptides, peptide-nucleic acids, oligosaccharides, antigens, immunoglobulins, cells, organelles, cell fragments, small molecules, chimeric molecules, and so forth. The following is a further description of various embodiments of the method of using MMA 10 in respect of different reagents. It is meant for illustrative purposes only and is not meant to be exhaustive of the methods of using MMA 10.

In a first embodiment of the method, MMA 10 is used for testing nucleic acid hybridations, such as DNAs, RNAs, cDNAs or other nucleic acids. For example, the first reagent may comprise DNA probes while the second reagent may comprise samples for testing. In the first step, first channel plate 14 having first microfluidic channels 18 arranged in first predetermined pattern 18A, such as a radial pattern, is sealed with test chip 12, such as an aldehyde glass slide. Next, solutions of aminated DNA probes are loaded into inlet reservoirs 22 and distributed through first microfluidic channels 18 using centrifugal force as described above. The DNA probes become immobilized onto test chip 12 due to Schiff-base linkage formed between amine and aldehyde groups. The DNA probes will form an array on test chip 12 in the same pattern as first predetermined pattern 18A. First channel plate 14 is then removed from test chip 12 and the procedure for reduction of Schiff-base linkages and excess aldehyde moieties is performed. Other methods for immobilizing or fixing the probes to the test chip 12 can also be used. In the second step, second channel plate 16 having second microfluidic channels 20 arranged in second predetermined pattern 20A, such as a spiral pattern, is sealed against test chip 12, and samples are introduced into inlet reservoirs 26 and distributed through second microfluidic channels 20 using centrifugal force. As the samples flow through second microfluidic channels 20 of second channel plate 16, the probes are exposed to the samples at test positions 30. Any samples which are complementary to any of the probes become hybridized at select test positions 32, thus indicating a positive test result. In the final step, detection of hybridization of samples on test chip 12, with or without removing second channel plate 16, is then conducted.

To detect hybridized samples on test chip 12, samples could be labeled, and only hybridized samples will remain bound to test chip 12 and be detected. For instance, the sample can be fluorescently labeled in which only the hybridized regions are fluorescent, or the sample can be biotin-labeled in which strept(avidin)-tagged microbeads, after binding, can be detected by reflectance measurement. Alternatively, a detection probe which interacts with hybridized samples only, but not to probes, could be used to detect hybridization. Other methods of detecting hybridized samples are known to persons skilled in the art.

A second embodiment of the method involves the use of MMA 10 to study cell-drug interactions.[23, 24, 25, 26, 27] For example, the first reagent may comprise different cell types while the second reagent may comprise different drugs to be studied. A priming reagent may also be used to prime the cells prior to exposing them to the different drugs, in the first step, first channel plate 14 is sealed with test chip 12. Different cell types are loaded into and distributed along first microfluidic channels 18 of first channel plate 14 using centrifugal force. The cells are immobilized to test chip 12 by adhesion or other methods. A Ca-sensitive florescent dye is flowed through first microfluidic channels 18 by centrifugal force and the cells become loaded with the dye. First channel plate 14 is then removed from test chip 12. In the second step, second channel plate 16 is sealed with test chip 12. Different drugs are introduced into and distributed along second microfluidic channels 20 of second channel plate 16 using centrifugal force. The cells are exposed to the drugs at test positions 30 and there may be positive reactions at select test positions 32. In the final step, cell-drug interactions can be detected by measuring cellular fluorescence. Other methods, of detecting cell-drug interactions are known to persons skilled in the art.

A further embodiment of the method involves the use of MMA 10 to study antibody-antigen interactions.[28] For example, the first reagent may comprise different antigen solutions while the second reagent, may comprise different antibody solutions. In the first step, first channel plate 14 is sealed with test chip 12. Different antigen solutions are loaded into and distributed along first microfluidic channels 18 of first channel plate 14 using centrifugal force. The antigens are immobilized to test chip 12. First channel plate 14 is then removed from test chip 12. In the second step, second channel plate 16 is sealed with test chip 12. Next, numerous fluorescently labeled antibody is introduced into and distributed along second microfluidic channels 20 of second channel plate 16 using centrifugal force. The antigens or antigenic peptides are exposed to the antibodies at test positions 30 and there may be positive reactions at select test positions 32. In the final step, binding of the antibodies with antigens or antigenic peptides is detected by measuring fluorescence. Other methods of detecting antibody-antigen interactions are known to persons skilled in the art.

A fourth embodiment of the method involves the use of MMA 10 to study oligosaccharide-protein interactions.[29, 30, 31] For example, the first reagent may comprise oligosaccharides (or carbohydrates or glycoproteins) while the second reagent comprises different proteins or cytokines. In the first step, first channel plate 14 is sealed with test chip 12. Different oligosaccharides are loaded into and distributed along first microfluidic channels 18 of first channel plate 14 using centrifugal force. The oligosaccharides are immobilized to test chip 12. First channel plate 14 is then removed from test chip 12. In the second step, second channel plate 16 is sealed with test chip 12. Different proteins are introduced into and distributed along second microfluidic channels 20 of second channel plate 16 using centrifugal force. The oligosaccharides are exposed to the different proteins at test positions 30 and there may be positive reactions at select test positions 32. In the final step, oligosaccharide-protein interactions can be detected by measuring fluorescence. Other methods of detecting interactions are known to persons skilled in the art.

A further embodiment of the method involves the use of MMA 10 to produce a small molecule array (SMA).[32, 33, 34] For example, the SMA can be used to observe the reaction between small molecules (R and S). Typically two steps are involved but an additional step is added if the enzymatic probing of the product formed from R and S is required. In the first step, first channel plate 14 is assembled with test chip 12. Next, solutions of small molecule (R) are loaded into and distributed along first microfluidic channels 18 of first channel plate 14 using centrifugal force. The small molecules (R) are immobilized to test chip 12. First channel plate 14 is then removed from test chip 12. In the second step, second channel plate 16 is sealed with test chip 12. Solutions of the second reactant (S) are introduced into second microfluidic channels 20 of second channel plate 16 using centrifugal force. At the test positions 30, product (P1) is formed. In the final step, the formation of P1 can be detected at select test positions 32 by enzymatic conversion to a colorimetric or fluorescent product using a common enzyme. Other methods of detecting the reaction products are known to persons skilled in the art.

Another embodiment of the method involves the use of MMA 10 for 2-D protein separations. Although 2-D separations have been exploited on microchips[35], these previous reports only employed a limited number of 2-dimension channels and solution filling y/as conducted by suction pumping which is subject to the problems associated with conventional fluid delivery techniques as discussed above. This invention improves microchip 2-D separation by not only increasing microfluidic channel density (e.g. the number of channels can be increased to 96), but by also employing a simple test, solution delivery method (i.e. centrifugal pumping). Furthermore, although both 2-D separations can be based on electrophoresis because of the ease of liquid flow in microfluidic channels using electrokinetic pumping, HPLC can also be conducted on the chip using non-electrical pumping based on centrifugal force. Thus, all electrophoresis, all chromatography[36] or first-electrophoresis-then-chromatography, can be carried out using the MMA platform described herein. In the case of chromatography, the stationary phase needs to be anchored to the chip, which can be achieved by forming UV-photopolymerized monoliths.

Figure 18:
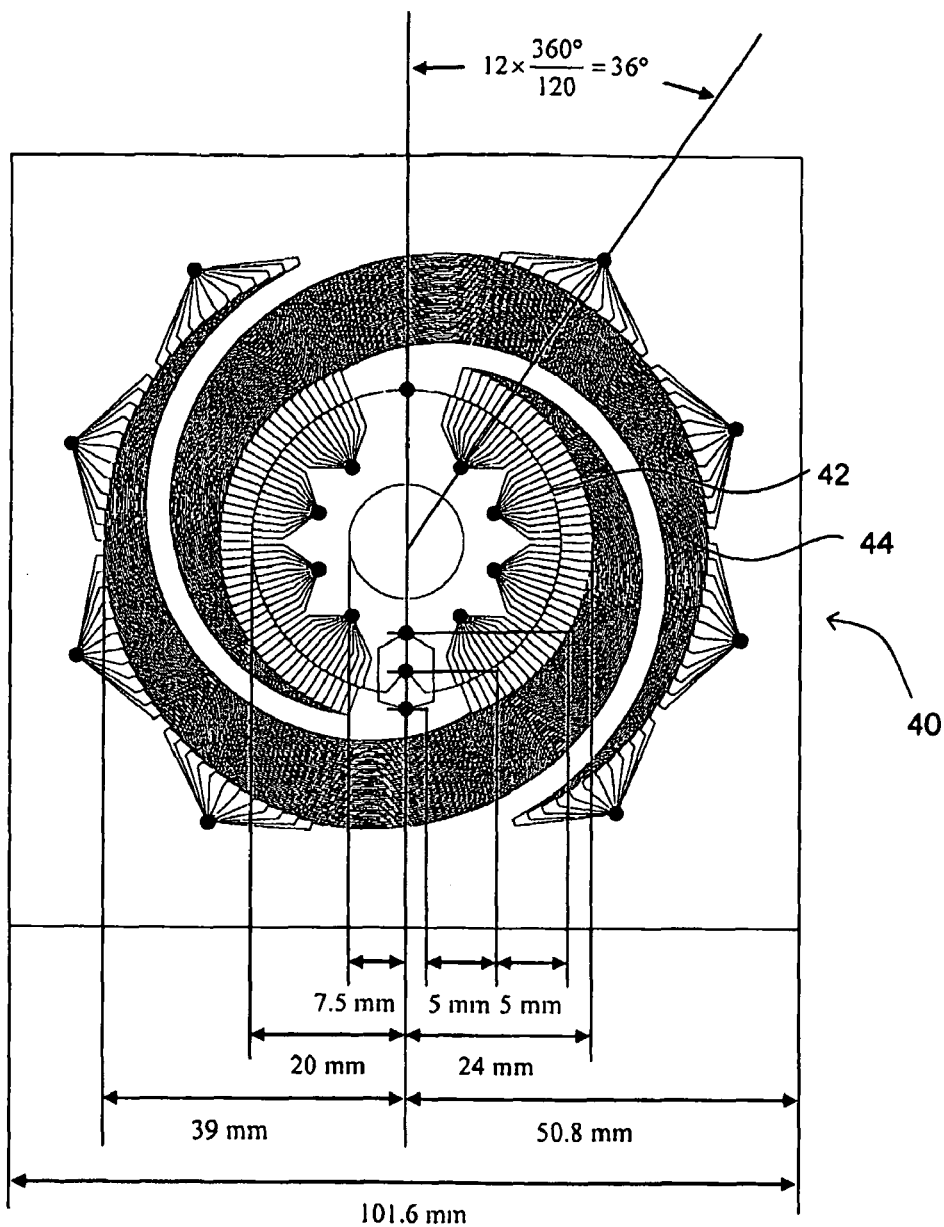
FIG. 18 is a schematic view of a single channel plate used for conducting 2-D protein separations.

With reference to FIG. 18, to conduct 2-D separations, MMA 10 may comprise a single channel plate 40 having two sets of microfluidic channels. The first set of microfluidic channels comprises a single circular microfluidic channel 42 while the second set of microfluidic channels comprises a plurality of spiral microfluidic channels 44. For high-density 2-D separations, centrifugal pumping is used to fill the plurality of spiral microfluidic channels 44 with gel media. Isoelectric focusing (IEF) is first done on single circular microfluidic channel 42 and SDS-PAGE (sodium dodeyl sulfate-polyacrylamide gel electrophoresis) is done on the plurality of spiral microfluidic channels 44. Alternatively, the method may involve applying IEF to single circular microfluidic channel 42 followed by applying centrifugal force to the plurality of spiral microfluidic channels 44. This platform can be employed to conduct protein separations for proteomics application. The labeled proteins (lysoyzme, bovine serum albumin, actin, ovalbumin, paralbumin and trypsin inhibitor) or peptides (enkephalin, bradykinin, angiotensin peptides, cytochrome C tryptic digest) can then be detected by fluorescence measurements. The experimental conditions are based on microchip separations[37] and conventional separations such as chromatography[38] and electrophoresis[39, 40, 41, 42, 43, 44] which are known to persons skilled in the art.

In summary, the MMA 10 of the invention has many advantages, including, but not limited to, the following: (1) its low manufacturing cost, due to the inexpensive materials used to fabricate test chip 12 and channel plates 14, 16 and 40; (2) its applicability to different reagents, including oligonucleotides such as cDNA; (3) the ability to test multiple probes and multiple samples at the same time so that time and reagents can be saved, and experimental conditions (spotting and hybridization) are consistent to enhance reproducibility and reliability of results; (4) the volumes of probes and samples used are small; (5) the surface reactions (immobilization and hybridization) are fast because of the high surface-to-volume ratio; (6) the simplicity of using centrifugal force as a means to distribute reagents to test positions, thereby avoiding the disadvantages of photolithographic synthesis and reagent spotting techniques; the ability to create high density microarrays by avoiding the need for complicated liquid handling interfaces.

EXAMPLES

The following examples will further illustrate the invention in greater detail although it will be appreciated that the invention is not limited to the specific examples.

Example 1

Figure 6:
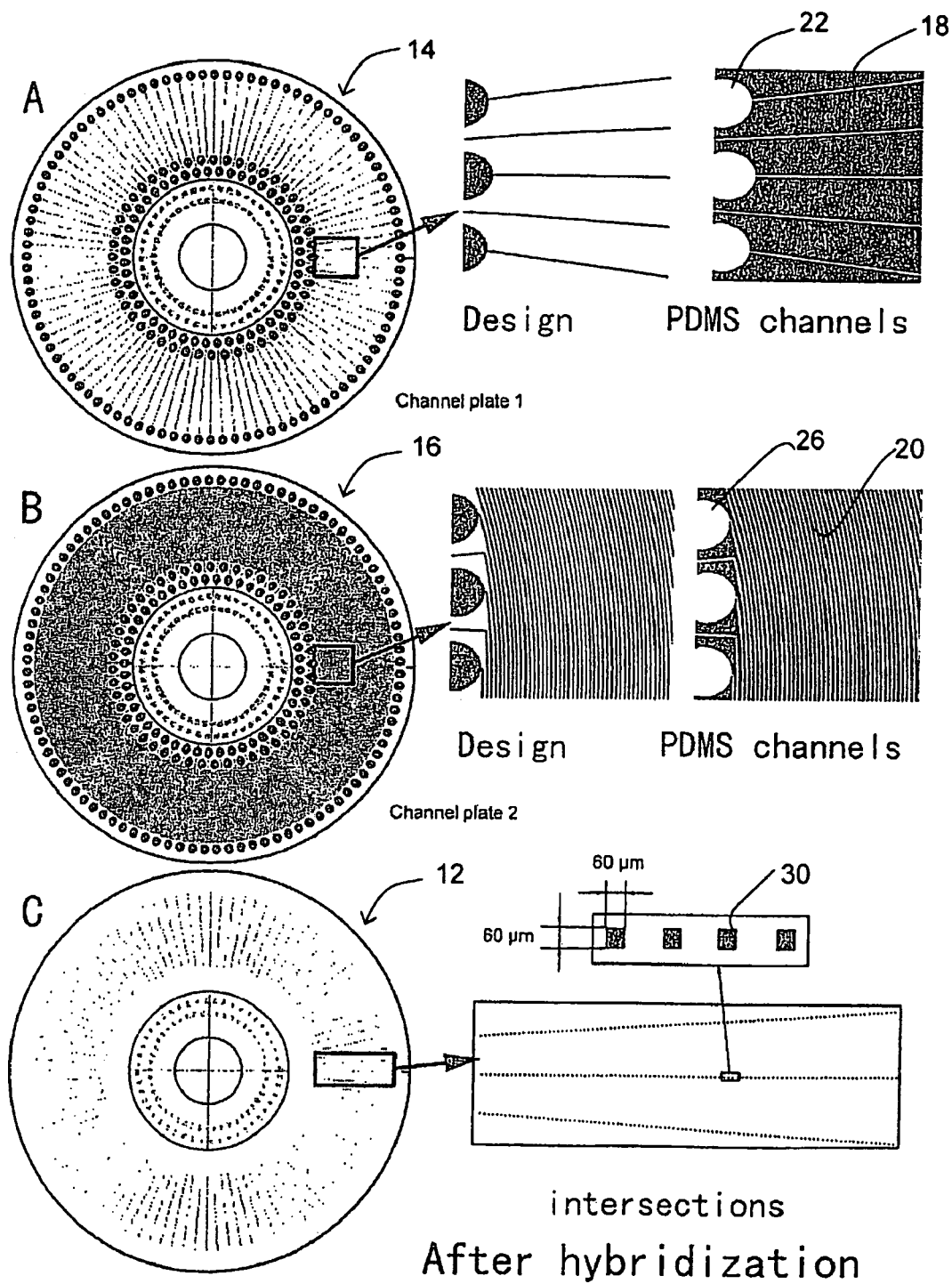
FIG. 6(A)-(C) are schematic view showing the fabrication of a microarray device for use in detecting DNA hybridizations. (A) First channel plate. The inset shows the radially extending first microfluidic channels and the actual appearance of a plurality of PDMS channels. (B) Second channel plate. The inset shows the spirally extending second microfluidic channels and the actual appearance of a plurality of PDMS channels. (C) Test chip. The inset shows the discrete test positions located at the intersections between the radial and spiral fluid distribution patterns.

DNA Hydridization 1.1 The Channel Plates for the Creation of a 96*96 Hybridization Microarray FIG. 6 shows the design of first and second channel plates 14, 16 in one embodiment of MMA 10. In FIG. 6A, first channel plate 14 has 96 microfluidic channels 18 for DNA probes arranged in a radial pattern. The left inset shows the molding master design of 5 microfluidic channels arranged in a radial pattern and the staggered, alternating positions of inlet reservoirs 22. The right inset shows the appearance of 5 PDMS microfluidic channels 18 formed from the molding master. In FIG. 6B, second channel plate 16 has 96 microfluidic channels 20 for samples arranged in a spiral pattern. The left inset shows the molding master design of the microfluidic channels arranged in a spiral pattern and the staggered, alternating positions of inlet reservoirs 26. The right inset shows the actual appearance of PDMS microfluidic channels 20 formed from the molding master. The size of the plate is 92 mm in diameter. Each reservoir has a diameter of 2 mm. Each channel has a width of 60 µm and a depth of 20 µm. Inlet reservoirs 22, 26 were placed in a staggered fashion to ensure that inlet reservoirs 22, 26 are not too closely spaced to allow for efficient sample application. FIG. 6C shows test chip 12. The maximum capacity of the hybridization microarray in this embodiment is 96*96=9216 test positions 30, which means it is possible to immobilize up to 96 different probes for hybridization with 96 different samples. In this embodiment, each test position spot 30 is actually a square of 60*60 µm$^2$. The number of test positions 30 can be greater if a larger diameter chip (e.g. 120 mm) is used.

The fabrication procedure of the two channel plates 14, 16 in this example is described as follows. 1. The design of the radial and spiral microfluidic channel patterns 18A, 20A is created using VISUALBASIC. 2. The design bitmap file is sent to a 3386-dpi laser printer (Abacus printing) for printing on a plastic transparency to create a photomask. 3. The photomask is used for photolithography on a photoresist/silicon dioxide-coated 4" Si wafer. 4. The exposed and developed coated Si wafer is etched by buffered hydrofluoric acid (HF) (buffered oxide etch (BOE)) to create positive relief structures (20 µm high) on the Si molding master. The Si wafer was silanized for easy mold release. 5. Polydimethylsiloxane (PDMS) prepolymer (Corning Sylard 184) was casted on the Si molding master and cured at 60° C. for 1 h.[45] This produced channels measuring 60 µm at the top and 100 µm at the bottom. 6. Solution reservoirs (2 mm in diameter) were created on the channel plates by punching the PDMS layer using a flat-tip syringe needle hole puncher.

Figure 7:
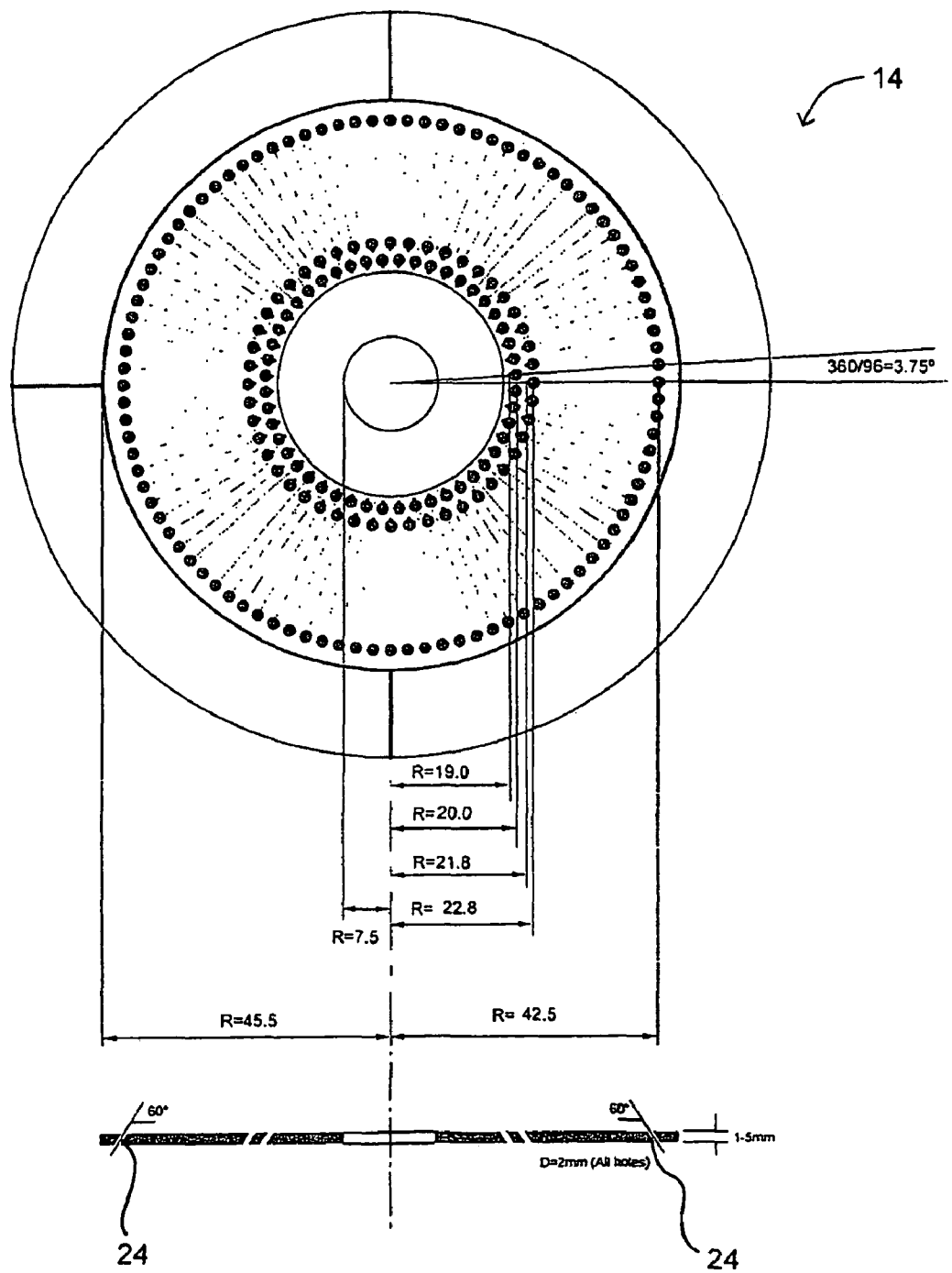
FIG. 7 shows the dimensions of an embodiment of a first channel plate having a radially extending fluid distribution pattern, including a cross-section of the plate.
Figure 8:
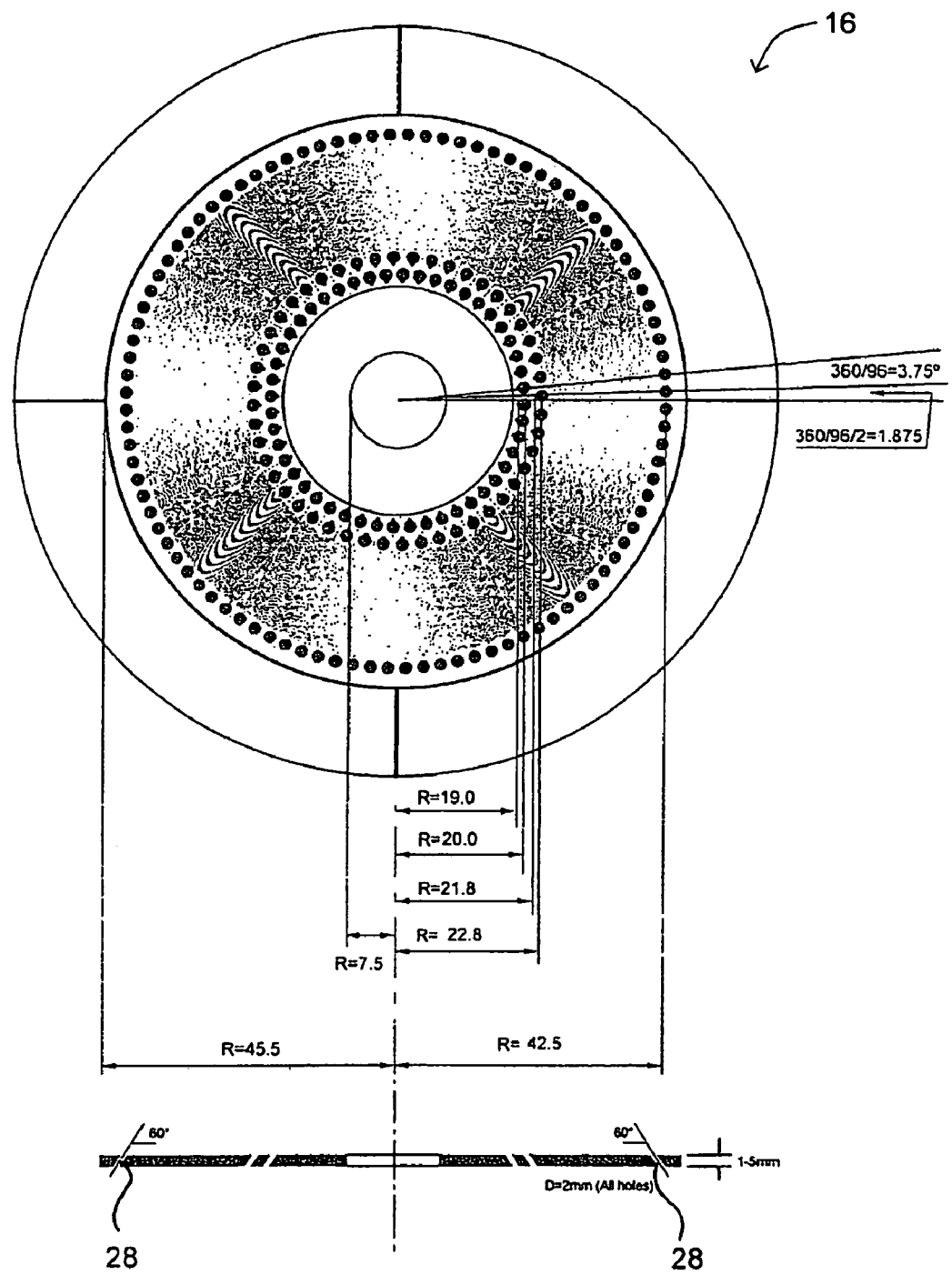
FIG. 8 shows the dimensions of an embodiment of a second channel plate having a spirally extending fluid distribution pattern, including a cross-section of the plate.
Figure 9:
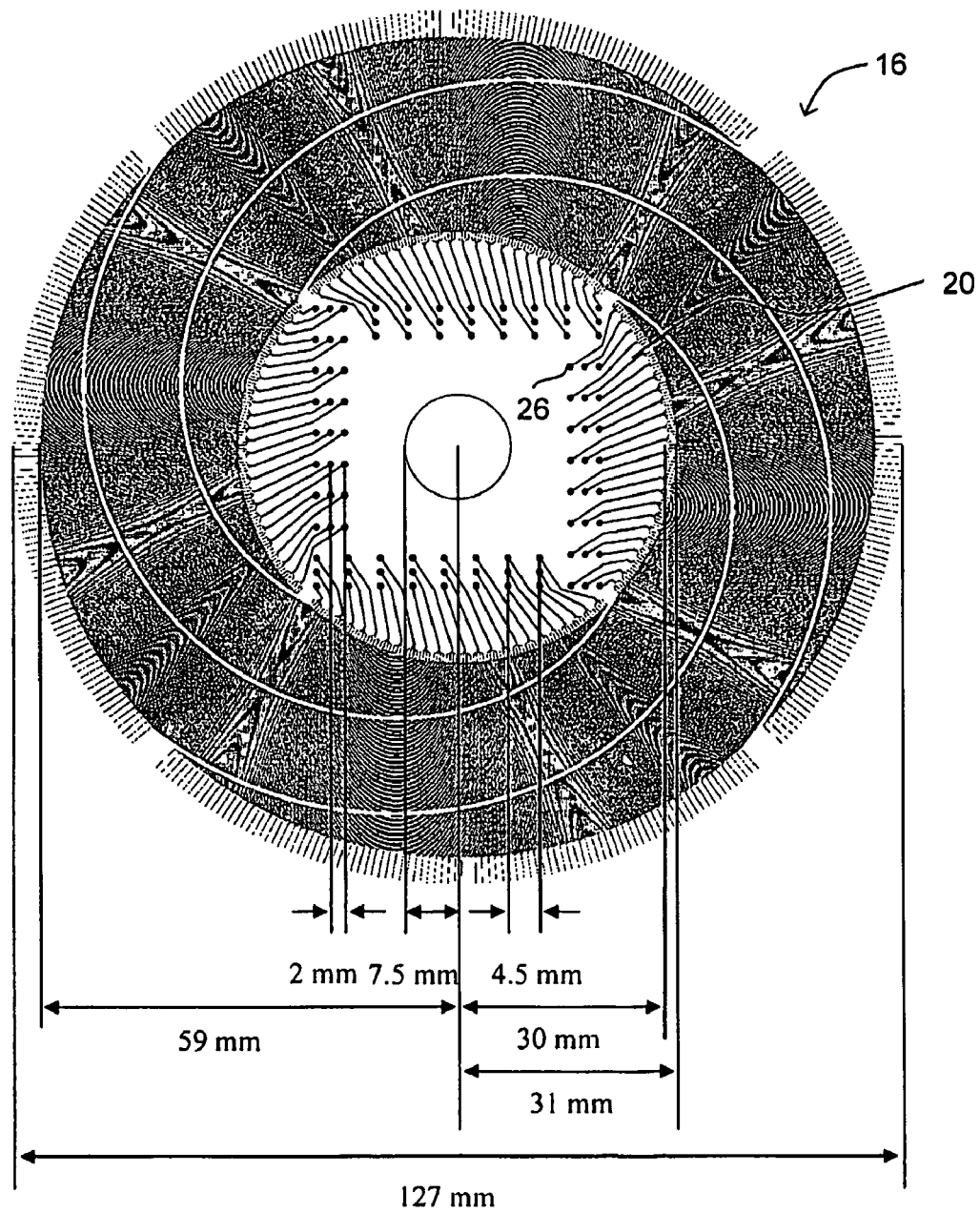
FIG. 9 shows the dimensions of an alternate embodiment of second channel plate.

The dimensions of first and second channel plates 14, 16 in this embodiment of MMA 10 are shown in FIGS. 7 and 8, respectively. Other dimensions of first and second channel plates 14, 16 can be used and these would be readily understood by persons skilled in the art. For example, FIG. 9 shows an alternative second channel plate 16 with different dimensions.

To ensure mat all the liquids in inlet reservoirs 22, 26 are distributed into first and second microfluidic channels 18, 20 without spillage, and are retained in outlet reservoirs 24, 28 while spinning the chip, inlet and outlet reservoirs 22, 26, 24, 28 may be produced at an oblique angle (for example, <90° relative to the central axis of the channel plate), as shown in the cross-sections of first and second channel plates 14, 16 in FIGS. 7 and 8.

1.2 The Test Chip

Test chips 12 were made from CD-like glass chips obtained from Precision Glass & Optics. They were 4" in diameter with a 0.6" centre hole. In this embodiment of MMA 10, test chip 12 is an aldehyde-functionalized glass chip (diameter, 100 mm) prepared as follows[46]: 1. The chip is thoroughly cleaned. 2. The chip is treated with aminopropyltriethoxysilane (APTES). 3. The chip is treated with glutaraldehyde. As would be readily understood by persons skilled in the art, other immobilization chemistries (e.g. thiol-gold, succinimidyl ester-amine, strept(avidin)-biotin) can be used to attach the DNA probes on the chip surface.

1.3 Buffers

In this embodiment, the probe immobilization buffer contains 0.15M NaCl, 0.1 MNaHCO$_3$, pH 8.5. The hybridization buffer contains 1×SSC, 0.015% SDS. Other buffers and methods for immobilizing probes and hybridizing samples are known to persons skilled in the art.

1.4 Spinning Devices

To initiate liquid flow by centrifugal force, MMA 10 can be mounted on a rotating platform. The platform rotation can be controlled by a variable-speed motor in which the rotation per revolution (RPM) has been calibrated.

1.5 DNA Probes and Samples

The probe sequences A and B used in this example have previously been used to detect plant pathogens *Didymella bryoniae* (A=D6 or CGCCGATTGGACAAAACTTAAA) and *Botrytis cinerea* (B=B1 or CGCCAGAGAATAC-CAAAACTC).[47] The 5'-end of probes A and B were conjugated to amine groups with a C6 linker. The probes were obtained from Sigma-Genosys (Oakville, ON).

To confirm probe immobilization, fluorescein-labelled probes A was used as a control. The DNA sequence is 5'-amine-C6-CGCCGATTGGACAAAACTTAAA-fluorescein-3'.

Four samples were used in this example: 1) a DNA sample (A') which is complementary to probe A labeled with fluorescein at the 5' end; 2) a DNA sample (A') which is complementary to probe A labeled with Cy5; 3) a DNA sample (B') which is complementary to probe B labeled with fluorescein at the 5' end; and 4) a DNA sample (B') which is complementary to probe B labeled with Cy5. Samples were also obtained from Sigma-Genosys (Oakville, ON).

1.6 Dynamic DNA Hybridization

First PDMS radial channel plate 14 was sealed with glass test chip 12 for DNA probe immobilization. Aminated DNA probes (2 µl, 100 µM) in immobilization buffer were applied to all inlet reservoirs 22 for DNA immobilization (500 RPM for 40 min., room temperature). Then, the chip surface was reduced (NaBH4 50 mg, 95% EtOH 10 ml, PBS 30 ml, 500 RPM for 15 min.), and then washed successively by 0.3% SDS (5 min), water (70° C., 5 min), and dried by N2.

After removing first radial channel plate 14 from test chip 12, second PDMS spiral channel plate 16 was sealed with test chip 12, and the resulting MMA 10 was spun (1800 RPM for 3 min.) on the rotating platform in a temperature controlled box. Cy5-labeled DNA samples (A' and B'), in hybridization buffer were added to all inlet reservoirs 26 for hybridization.

1.7 Hybridization Results

After probe immobilization and DNA hybridization, the microarray of test positions 30 generated on MMA 10 was detected fluorescently using a confocal laser fluorescent scanner (resolution 10 µm, Typhoon 9410, Molecular Dynamics, Amersham Biosystems).

Figure 12:
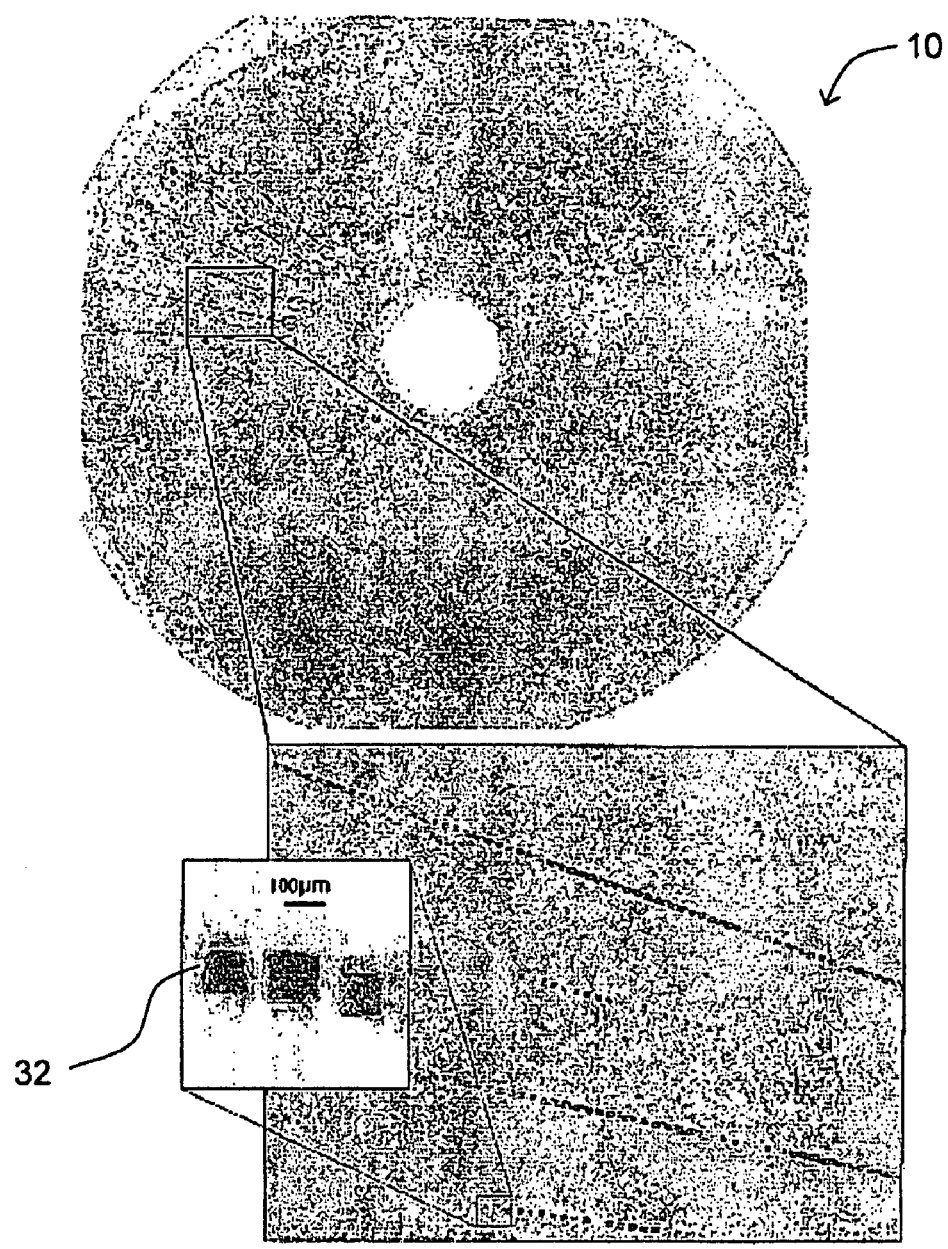
FIG. 12 is a photograph showing hybridization tests conducted in one embodiment of a microarray device fabricated in accordance with the invention. The image of the whole device depicts 6 radial lines of probe A, showing successful probe immobilization. The first inset shows the test positions formed after successful hybridization of probes and samples loaded in the microarray device. The second inset is a magnified view of 3 discrete square-shaped test positions.

FIG. 12 shows the hybridization results on test chip 12. Only 11 radial microfluidic channels 18 were loaded with aminated probes. The 6 dark lines represent the 6 radial microfluidic channels where the immobilization control, flourescein-labelled probe A, was loaded. The non-fluorescent probes were loaded in radial microfluidic channels 18 located between these 6 radial microfluidic channels, the inset shows that 22 spiral microfluidic channels 20 were loaded with samples. The spots at select test positions 32 show the locations where hybridization has occurred. In this inset, the two dark lines represent the immobilization control. The middle radial microfluidic channel in between the two dark lines represents hybridization between probe B and various samples. The bottom radial microfluidic channel below the bottom dark line represents hybridization between probe A and various samples. A magnified inset further shows select test positions 32 resulting from hybridization between the sample A' and probe A. The hybridization conditions are not optimized, and this figure only serves to illustrate the various steps used to hybridize probes and samples using this embodiment of MMA 10.

Figure 10:
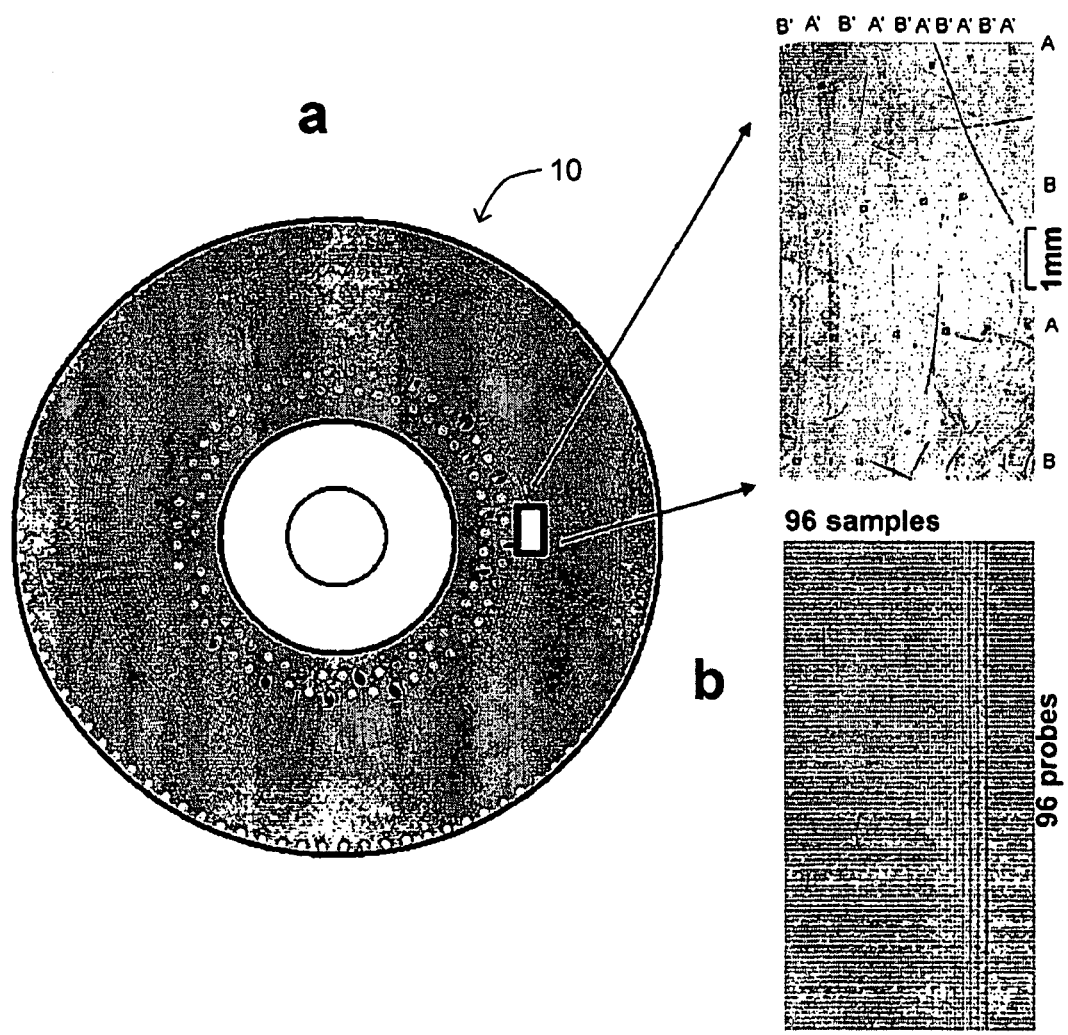
FIG. 10 shows hybridization results on a microarray device. The sequences of the DNA probes (A and B) and the DNA samples (A' and B') are shown, (a) Fluorescent image of specific hybridizations between nucleic acid reagents. The right inset shows a portion of the microarray test positions indicating specific hybridization, (b) The rectangular array obtained after image transformation.

FIG. 10 shows the results of hydrodynamic hybridization performed on MMA 10 using spiral microfluidic channels. The inset of FIG. 10a shows a section of the microarray of test positions 30 produced by this embodiment of MMA 10. The sequences of the DNA probes (A and B) and DNA samples (Cy 5-labeled A' and B') are given. The vertically oriented spiral microfluidic channels have been alternately filled with Cy 5-labeled DNA samples, A' and B'. A' and B' are oligonucleotides having sequences complementary to A and B, respectively, as shown in the upper part of the figure. Where A' binds to A, the hybridized oligonucleotides appear as a dark square spot, and where B' binds to B, the hybridized oligonucleotides also appear, as a dark spot. Dark spots do not appear where the labelled sample has not hybridized. Cross reactions (i.e. between A and B', and between A' and B) are not seen.

The microarray image as obtained from the circular test chip 12 does not conform to the usual rectangular format of microarray data. Therefore, image transformation has been performed (see FIG. 10b). The circular microarray generated by MMA 10 is mathematically transformed into a rectangular array. The 8-bit pixel values at the definite microarray locations are read by a computer and these values are mapped to a 96×96 rectangular array, using software. Each small image representing each test position 30 is of the same intensity as in the original circular image, except that the distance between adjacent test positions 30 is shorter than the real distance on the CD.

Figure 11:
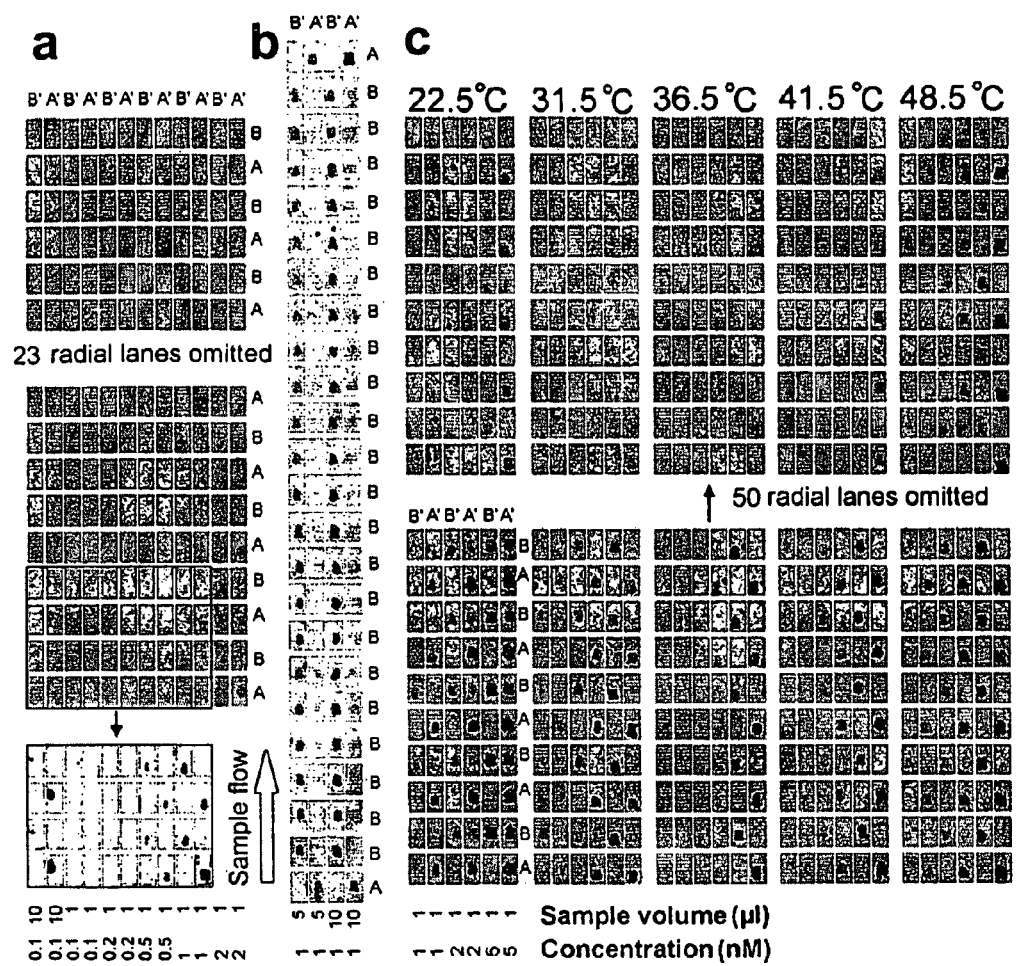
FIG. 11 shows hybridization results presented in rectangular format, (a) Hybridizations at room temperature by various sample concentrations (0.1-2 nM) and volumes (1 or 10 μL) for the study of sample utilization and detection limits. The rows, represent the probes (A and B) first immobilized via the radial microfluidic channels (horizontal); whereas the columns represent various samples (A' and B') introduced via the spiral microfluidic channels (vertical) in the flow direction given by the hollow arrow. The bottom inset shows the hybridization results in the boxed region but scanned at a higher detector sensitivity, (b) Hybridizations of sample A' to probe A, but without repeated hybridizations over 22 sites of probe B. The sample concentration is 1 nM, and the sample volumes are 5 or 10 μL. (c) Hybridizations of 6 columns of samples obtained at 5 temperatures (22.5, 3.1.5, 36.5, 41.5 and 48.5° C.). The arrangements of sample volume (1 μL) and concentration (1, 2 and 5 nM) in all blocks are the same as in the left lowermost block.

A section of FIG. 10b is expanded and shown in FIG. 11a to illustrate more detail of the hydrodynamic hybridization. The horizontal rows represent DNA probes immobilized in an alternating pattern, i.e. A and B in alternating rows. The vertical columns represent alternate patterns of labeled DNA samples, i.e. A' and B' in alternating columns. The DNA samples are applied at different. DNA concentrations and sample volumes, as shown. Here, specific hybridizations were easily observed for the sample (2 nM, 1 μL), see the right 2 lanes of FIG. 11a. When the sample concentration is 1 nM, specific hybridizations were still observed (see the bottom inset of FIG. 11a) after image enhancement. The lowest concentration observed is 0.5 nM at 1 μL. To improve the detection limit, a greater sample volume (i.e. 10 μL) was used. In both cases, i.e. 1 μL of 1 nM or 10 μL of 0.1 nM, the mass defection limits are the same, i.e. 1 fmol, all attained in 3 min. of hybridization. The high detection sensitivity and fast hybridization rate can be explained by the short diffusion distance and high surface area achieved in microfluidic channels, as previously studied by other groups.[48, 11, 49]

In these hydrodynamic hybridization results, it is observed that the intensities near the inlet regions of the spiral microfluidic channels are higher and the intensities at the latter part of the microfluidic channel are lower, see the right 2 lanes in FIG. 11a. This observation could be explained by the fact that the sample (i.e. A' in the rightmost channel) was repeatedly hybridized with the same probe (e.g. A' to A), and hence the sample was reduced in concentration, causing a gradual reduction in fluorescent intensity of subsequent hybridizations. This effect due to sample consumption actually illustrates, the high and efficient utilization of the small volume of the DNA sample. On the other hand, if there were no hybridizations, the DNA sample concentration would not be reduced, and the fluorescent intensity would be unchanged. This is confirmed in FIG. 11b where the rightmost sample A', after passing by 22 probes of B, still produces the same intensity with another probe A. It is noted that in the 2nd right lane of FIG. 11b, the intensities of sample B' gradually decreased as it sequentially hybridized with the same probe B. The repeated hybridizations will not be encountered in the usual situation where multiple samples and probes are used.

Hydrodynamic hybridizations in microfluidic channels have also been carried out at higher temperatures (FIG. 11c). It was noted that the non-specific hybridization obtained at 22.5° C. disappeared when higher temperatures (31.5° C., 36.5° C., 41.5° C. and 48.5° C.) were used. Moreover, by comparing the hybridization results of the earlier part of the spiral channel (bottom of FIG. 11c) with those of the latter part (upper of FIG. 11c), it was found that the signal (at 48.5° C.) was not reduced as the sample flowed near the outlet. This observation was attributed to the fact that non-specific hybridization is reduced at a higher temperature, thus allowing sufficient samples to bind the complementary probes.

Example 2

Fluid Flow Velocity in the Spiral Microfluidic Channels

Figure 13:
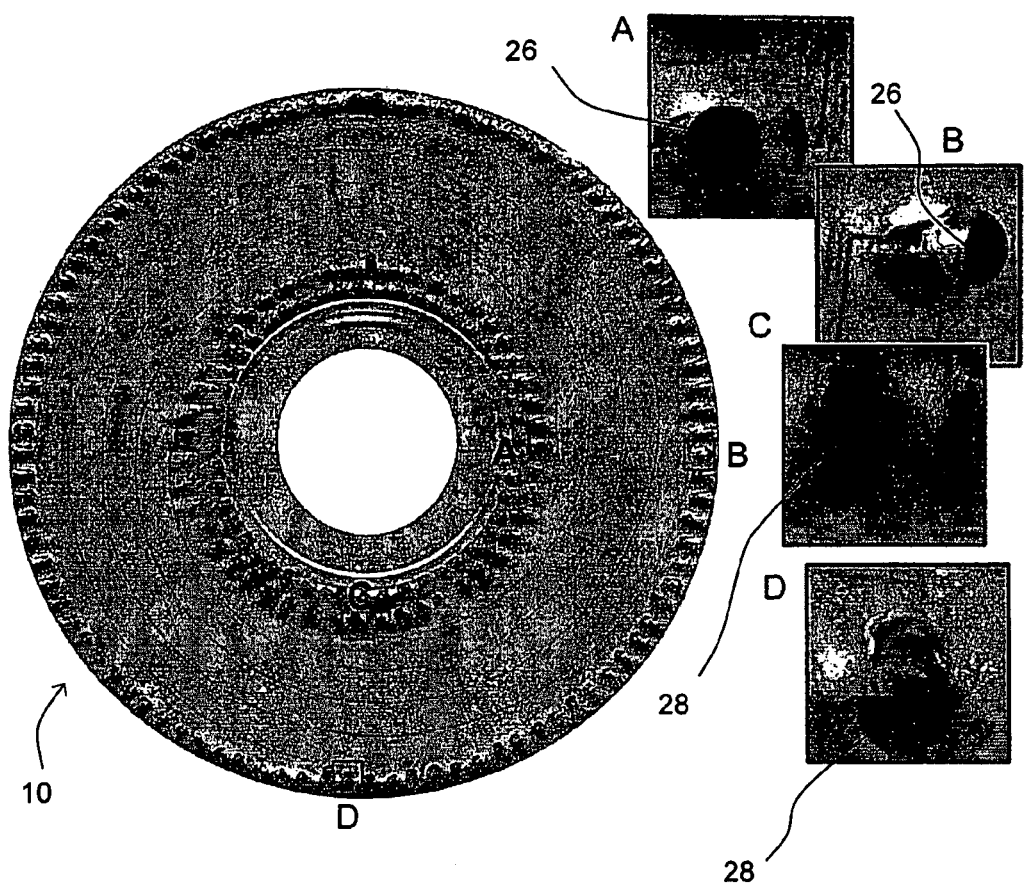
FIG. 13 is a photograph of an embodiment of a microarray device comprising a second channel plate sealed with a test chip. Dyed solutions are loaded into four center inlet reservoirs and the device is spun. The insets show the appearance of two inlet reservoirs (A, C) and two outlet reservoirs (B, D).

Liquid was successfully filled into spiral microfluidic channels during spinning or rotation of MMA 10. The result is shown in FIG. 13 in which 4 spiral microfluidic channels were filled with solutions containing blue food dye (Scott-Bathgate, Vancouver, BC). In one spiral microfluidic channel, the solution flowed from inlet reservoir A to outlet, reservoir C, see inset. In another spiral microfluidic channel, the solution flowed from inlet reservoir B to outlet reservoir D, see inset. The microfluidic channels were illuminated by a stroboscope light (Monarch, Nova-Strobe DA Plus 115) at the same frequency as the rotation speed. Using the stroboscope light, the movement of the fluid in the microfluidic channels can be seen flowing even though the chip is spun at high speed.

To study the fluid velocity in the spiral microfluidic channels, the positions of the advancing liquid front meniscus during filling of the spiral microfluidic channels were recorded by a video camera (Sony, DCRTRV260) to determine the flow velocities when MMA 10 was spun at 2500 RPM. To assist in position measurement, 96 radial lines were drawn on a piece of paper and put under the glass chip. Each image frame of the video clips was studied and measured to determine the times and positions of the liquid fronts.

FIG. 14A shows the overlay of 96 traces of the transit time (t) plotted against the position of the advancing liquid front (L) in a spinning MMA 10 at 2500 RPM. The liquid front velocity is given by the reciprocal of the slope. In each trace, it is observed that the liquid front reaches the maximum constant velocity after travelling for 50 mm (see the constant slope reached after 50 mm), albeit the values are different in different microfluidic channels, possibly due to different microfluidic channel conditions. The attainment of constant velocity is only possible in the equiforce spiral microfluidic channels in which the centrifugal force component remains constant, for each liquid element along anywhere in the microfluidic channel. The slower initial liquid front velocity (or greater slope) was attributed to liquid surface tension (S) in the hydrophobic PDMS microfluidic channel, in which S was not sufficiently overridden by the centrifugal force due to the initially shorter liquid column. In FIG. 14B, the velocities in all 96 channels were plotted against the distance, and it is seen that the constant velocities in all microfluidic channels are within a range of 5±1 mm/s. Note that the velocity in each spiral microfluidic channel is constant within a much narrower range.

Based on a theoretical model, a flow equation relating the transit time (t) and the filling column length (L) has been derived and is given as follows $$t = \frac{k_2}{k_1}L + \frac{k_2(k_1 L_0 + S - F_0)}{k_1^2}\ln\left(L - \frac{S - F_0}{k_1}\right) + C' \quad (1)$$

where $L_0$ is initial straight channel length, S is surface tension and $F_0$ is centrifugal force due to liquid mass in $L_0$ (FIG. 14G); C' is the integration constant; $k_1$ and $k_2$ are lumped property constants. The derivation of equation (1) is described as follows.

FIG. 14G shows how a spiral microfluidic channel is connected to the inlet liquid reservoir. After the short straight channel ($L_0$), the channel changes its direction at an angle $\alpha_0$ to the radius along the spiral channel. The liquid in the reservoir is continually filled into the empty spiral microchannel.

The flow in the channel can be modeled by the Navier-Stokes equation, which results from the momentum conservation equation, and is formulated by a balance of the body force (centrifugal force), surface force (viscous drag force) and the pressure field.[50] The line force (surface tension effect) comes into play as a boundary condition at the liquid front meniscus. Under the conditions of a constant body force within the equiforce spiral channel, the model is simplified by directly using the force balance in a 1-dimensional approximation In this simplified model, the body force (F) is a linear accumulation of the constant centrifugal force of infinitesimal liquid elements within the spiral channel. F increases with the column length L (see also equation A12) and is given as follows:

$$F = k_1 L \quad (B1):$$

where $k_1$ is a constant given by $$k_1 = \rho X \omega^2 r_0 \cos \alpha_0 \quad (B2)$$

where $\rho$ is the liquid density; X is the cross-section area; $\omega$, $r_0$ and $\alpha_0$ have been given in equation A2. But the body force ($F_0$) due to the liquid in the constant initial straight channel section is considered to a constant given by $F_0 = \rho X \omega^2 r_0 L_0$.

The surface force ($F_2$) is also a linear accumulation of the viscous drag force of infinitesimal liquid elements, which increases linearly as the contact area of the liquid column becomes increasingly larger. The viscous drag force, $F_2$, is given by Newton's viscosity equation as follows:

$$F_2 = \mu A \frac{du}{dy} \quad (B3)$$

where $\mu$, is the viscosity coefficient; du/dy is the velocity gradient across the mean channel width (2y); A is the contact area of the liquid column layer and is equal to $Z(L+L_0)$ in which Z is the perimeter of the channel cross-section.

The velocity gradient du/dy is proportional to the maximum velocity (u=dL/dt) at the centre of the channel. In fact, it was the position of the centre of the liquid front that was measured as L in the experiments. Then, all constants are lumped into $k_2$ to give:

$$F_2 = k_2(L+L_0)\frac{dL}{dt} \quad (B4)$$

At the liquid front, the line force (S) which is the surface tension at the liquid front exists, and it is considered to be constant given by:

$$S = Z\gamma \cos \theta \quad (B5)$$

where Z has been previously defined as the perimeter of the channel cross-section; $\gamma$ is the surface tension of the liquid; d is the channel depth; $\theta$ is the contact angle.

For a constant liquid flow velocity, the forward driving forces ($F_0$ and F) must be balanced by the backward forces ($F_2$ and S) as follows:

$$F + F_0 = F_2 + S \quad (B6)$$

Combining equations B1, B4 and B6 gives:

$$k_1 L + b = k_2(L+L_0)\frac{dL}{dt} \quad (B7)$$

where $b = S - F_0$

For integration, equation B7 is transformed to give $$dt = \frac{k_2(L+L_0)}{k_1 L - b} dL \quad (B8)$$

After integration:

$$t = k_2 \left( \frac{L+L_0}{K_1} + \frac{b}{k_1^2} \ln(k_1 L - b) \right) + C \quad (B9)$$

where C is the integration constant. By substituting $S-F_0$ for b and lump all constants not associated with L into C', this results in equation (1).

The plot of transit time versus distance for one spiral channel is shown in FIG. 14C. Using regression analysis, the data was fitted to equation 1 to give t=0.136+3.599 log (L−0.476)+0.272. The agreement (R=0.9995) between the experimental data (circles) and the fitted curve is excellent.

Subsequently, various sensitivity tests were performed in order to determine the optimal conditions to reach a constant flow velocity even as early as in the initial section of the spiral microfluidic channel. For instance, when the surface tension S was decreased (down to 1/32 of the original value), the linearity of the curve was increased (FIG. 14D), indicating that the constant flow velocity was attained over most parts of the spiral microfluidic channel. In the case of modifying S, the flow velocity (as given by the reciprocal of the slope) did not change greatly, as was evident from the parallel lines, indicating that there was no sacrifice in the flow time.

When the viscosity coefficient ($\alpha$), was reduced (down to 1/32 of the original value), the linearity of the curve was also enhanced (FIG. 14E), indicating the achievement of constant flow velocity in most parts of the spiral channel. However, the flow velocities became increasingly higher, as evident from the reduction in slopes. This would require the reduction in the spinning speed of MMA 10 in order to maintain the same flow velocity and reaction residence time. When the driving centrifugal force F was increased, the linearity of the curve was increased (FIG. 14F), but the flow velocities became higher and higher.

Based on these sensitivity tests, some ways to expand the range of constant velocity was identified. For instance, MMA 10 can be spun faster or a larger sized test chip 12 can be designed to generate a stronger centrifugal force to overcome the surface tension barrier. Nevertheless, this stronger centrifugal force generates a higher flow velocity, and so there is insufficient time for hybridization to complete. The best way is to use a surfactant to decrease the surface tension barrier. This method does not result in any increase in the flow velocity (see FIG. 14D), and the range of constant flow velocity can be expanded to nearly the whole microfluidic channel. In experiments, surfactant (0.015% SDS, normally used in hybridization solution) was applied in the sample solution. The hybridization finished in 3 min. (at 1800 RPM) for each probe.

Example 3

Cellomics Studies Using the MMA

Cell-based assays can also be conducted using MMA 10. The assays may be carried out using a batch of cells or single cells. The National Cancer Institute (NCI) has identified a total of 60 cancer cell lines, (NCI-60), which can be exposed to thousands of compounds for drug discovery.[51] These cell lines are related to specific cancers: Lung (e.g. A549), Colon (e.g. HT29), Breast (e.g. estrogen-sensitive MCF7 and estrogen-insensitive MDA-MB-231), Ovarian, Leukemia (e.g. Jurkat), Renal, Melanoma, Prostate and Central Nervous System.

In these experiments, test chip 12 is arrayed with cells which are exposed to various drugs at different concentrations. For instance, 60 cells lines can be constructed as a cell microarray on a glass surface test chip 12 and hundreds of chemicals can be exposed to the cells at one time under the same flow and media conditions. For proof of concept, the 4 above cell lines, which are of biosafety level 1, are selected for testing with various drugs (taxol, ginsenoside, doxorubicin) at various concentrations.

There are 2 issues that have to be addressed in creating a cell microarray. First, the cells have finite thickness, e.g. 10 μm. Therefore, the presence of a line-array of cells may create a leakage problem when second channel plate 16 is sealed against test chip 12. This issue is addressed by creating a discontinuous cell array, rather than a continuous line-array as will be discussed in more detail below. Second, the cells require a cell medium to remain viable, with the result that the cell line-array is not as robust as a DNA line-array. This issue is addressed by encapsulating the cells in a cell viability promoting material, such as a hydrogel layer. As previously reported, the encapsulated cells remain viable and small molecules can diffuse through, the polymeric hydrogel layer to interact with the cells.[52, 53]

Accordingly, the assembly process involves 4 steps in this example, rather than 2 steps (FIG. 15). This involves the alignment of first and second channel plates 14, 16 and first and second masks 34, 36 with test chip 12. In the first step, the locations of the cells is determined by defining cell-adherent and non-adherent domains. A microcontact stamping process is adopted.[54] First mask 34 having a plurality of microfluidic channels arranged in second predetermined reagent pattern 20A, such as a radial pattern, is stamped with a cell non-adherent solution, such as poly(L-lysine)-graft-poly(ethylene glycol), in the areas of first mask 34 where microfluidic channels are not located. First mask 34 is then assembled with test chip 12, such as a glass chip. The cell non-adherent solution is transferred to test chip 12 at the points where first mask 34 is sealingly connected to test chip 12. A cell adhesion solution (e.g. fibronectin) is flowed in the radial microfluidic channels of first mask 34. This results in cell non-adherent domains at the sealed locations, and the cell adherent domains at the radial microfluidic channel locations of first mask 34. First mask 34 is then removed. In the second step, first channel plate 14 having, first microfluidic channels 18 arranged in a first predetermined reagent pattern 18A, such as a spiral pattern is sealed to test chip 12 (in this example the first predetermined reagent pattern is a spiral pattern and the second predetermined reagent pattern is a radial pattern). Cell suspensions are introduced into first microfluidic channels 18. The cells can only adhere to test chip 12 at the intersection points between first predetermined pattern 18A and second predetermined pattern 20A previously defined by the microfluidic channels of first mask 34. First channel plate 14 is then removed. In the third step, second mask 36, such as a UV photomask, having a plurality of microfluidic channels arranged in second predetermined reagent pattern 20A, such as a radial pattern, is sealed to test chip 12. A cell viability promoting material, such as a hydrogel monomer solution, is flowed into second mask 36 microfluidic channels and is cured at the cell domains. Second mask 36 is then removed. In the final step, second channel plate 16 having second microfluidic channels 20 (which are wider than first mask 34 microfluidic channels) is sealed with test chip 12. The cell domains which are enclosed in the second microfluidic channels 20 are ready for experiments to determine cell-drug interactions. For example, different drugs may be loaded into and distributed through second microfluidic channels 20 of second channel plate 16.

For measurement of cellular responses for detection purposes, one method is to use live cells that will react with -(4,5-dimethylthiazol-2-yl)-2,5 diphenyltetrazolium bromide (MTT) in a cell inhibition study to produce formazan.[55] These colored products are formed in the presence of live mitochrondia dehydrogenase and are directly observed in the cell domains using a scanner.

Alternatively, the cells can be pre-labelled with a Ca2+-sensitive probe. However, some experiments with Ca2+ flux assays[56, 57] indicate that they are transient in nature and thus are not amenable to experiments in which the measurements are performed at a later time. Therefore, a third method, the reporter gene assay, which is based on green-fluorescent protein (GFP) can be used. In this case, the cellular response is provided by expression of GFP which can be visualized even after the drug stimuli are removed. This method requires cell transfection, but it can be conducted in step 2 in which first channel plate 14 is sealed to test chip 12. The transfection is carried out after the cells have been introduced into and distributed through first microfluidic channels 18 of first channel plate 14. This allows for different transfection vectors to be used for different cells. The transient transfection of the Iκβ-EGFP vector into Jurkat cells for an on-chip study have been reported.[58] This vector is involved in the NFκβ pathway that has been used as a drug screening platform for discovery of anti-cancer drugs.[59]

Example 4

Small-Molecule Microarray (SMA) for Enzyme Binding

MMA 10 of the invention can be used to create a SMA with numerous different compounds on its surface. The compounds may be made using diversity-oriented synthesis[60] and can be used to study the binding event of cellular proteins, such as Ure2p, which is involved in nitrogen metabolism[61]. By exposing a high-density SMA of 1,3-dioxane-based small molecules with fluorescently labeled Ure2p, thousands of protein-binding assays can be performed in parallel and this has identified several Ure2p-binding compounds such as uretupamine.

The 1,3-dioxanes are generated from a split-pool synthesis by a three-step reaction as shown in FIG. 16. Normally, these small molecules are created by solid-phase synthesis on beads. The compounds are then cleaved and spotted onto slides to form a microarray. Using MMA 10 of the invention, the compounds may be synthesized on test chip 12 and then used directly after, synthesis within the microfluidic channels, thus avoiding the cleavage step. Originally, an acid and a base stable diisopropylphenylsilyl ether linker was formed to permit mild fluoride-mediated cleavage of the small molecules from the beads. This linker may either be retained, but without using the cleaving step, or another non-cleavable linker, such as glutaraldehyde, may be employed. Three distinct γ,δ-epoxy alcohols (R1) were attached to the linker (see FIG. 16). First, the epoxy alcohols were reacted with a diverse set of 30 amine and thiol compounds (R2) to generate 90 different 1,3-diols (4). Second, they were reacted with 2 Fmoc-aminodimethyl acetal building blocks to furnish 180 Fmoc-amino-1,3-dioxanes (5). Third, these 1,3-dioxanes were reacted with 10 electrophiles (R3) to generate 1800 amides, ureas, thioureas, and sulfonamides (6). The table in FIG. 17 summarizes this synthesis of a 1,3-dioxanes library using MMA 10. In this case, the synthesis of these 1800 small, molecules is to be achieved on the 96 radial and 96 spiral microfluidic channels.

In this experiment, test chip 12 is a glass chip which is first amino-coated using aminopropyltriethoxysilane (APTES). In the first step, first channel plate 14 having radial microfluidic channels 18 is sealed with test chip 12. The linker molecule (O) is then introduced by flowing it through all 96 radial microfluidic channels (Initial stage 1). The 96 microfluidic channels will be divided in 3 regions, 32 each. Next, each region is flowed with a different epoxy alcohol (compound a), creating $Oa_1$, $Oa_2$, $Oa_3$ in the three regions (Initial stage 2). Test chip 12 is now ready for the 3-step chemical reactions as follows. In each group of the 32 radial microfluidic channels 18, 30 of them are introduced with different amine/thiol (compound b) for reactions to form 1,3-diols (Reaction 1). The remaining two channels are used as controls (see below for compound verification). First channel plate 14 is removed. In the second step, second channel plate 16 having spiral microfluidic channels 20 is sealed with test chip 12. A first group of 48 spiral microfluidic channels 20 is loaded with compound $c_1$ and a second group of 48 spiral microfluidic channels 20 is loaded with compound $c_2$: (Reaction 2). This generates two groups of 30*48 different compounds at the intersection points or test positions 30 between second spiral microfluidic channels 20 and the line array created by first radial microfluidic channels 18. To each of the 2 sets of 48 spiral microfluidic channels 20, 10 compounds d are added in 4-replicates totaling 40 microfluidic channels 20, with 8 microfluidic channels 20 used as controls (Reaction 3). After the completion of the reaction scheme, no cleavage is needed because the small molecule microarray is already on test chip 12, which is ready for screening by fluorescently labeled Ure2p in second spiral microfluidic channels 20.

The PDMS material used to form the microfluidic channels may degrade when exposed to some organic solvents.[62] This issue may be addressed by applying a solvent-resistant coating on the PDMS. For instance, a polymeric parylene coating deposited on PDMS has been reported to increase the solvent-resistant property of the microfluidic channels.[63] Verification of the formation of these 1,3-dioxanes can be performed by analyzing the compounds formed in the control microfluidic channels 20 by exploiting the cleavable linker. To do this, after the completion of the reaction scheme, the compounds formed in the control microfluidic channels 20 can be cleaved and transferred for analysis using LC-MS. It is noted that if control microfluidic channels are not used, the full capability of this MMA is the formation of 96×96=9216 small molecules. As appreciated by persons skilled in the art, other small molecules and other protein-small molecule screening reactions can be developed.

As will be apparent to those skilled in the art in the light of the foregoing disclosure, many alterations and modifications are possible in the practice of this invention without departing from the spirit or scope thereof.

REFERENCES

[1] Fodor S P A, Read J L, Pirrung M S, Stryer L, Lu A T, Solas D, "Light directed spatially addressable parallel chemical synthesis", Science, 251 (1991) 767-773.

[2] Campas, M.; Katakis, I. DNA Biochip arraying, detection and amplification strategies. *Trends Anal. Chem.* 2004, 23, 49-62.

[3] Werner, M. E.; Valencia, R. M.; Virtanen, A. J.; Zoval, J. V. "Surface Assembly for Immobilizing DNA capture probes and bead-based assay including optical bio-discs and methods relating thereto", US Patent Application 2002/0168652.

[4] Liu, Y.; Rauch, C. B.; Stevens, R. L.; Lenigk, R.; Yang, J.; Rhine, D. B.; Grodzinski, P. DNA amplification and hybridization assays in integrated plastic monolithic devices. Anal. Chem. 2002, 74, 3063-3070.

[5] Wang, Y; Vaidya, B.; Farquar, H. D.; Stryjewski, W; Hammer, R. P.; McCarley, R. L.; Soper, S. A.; Cheng, Y.-W.; Barany, F. Microarrays Assembled in Microfluidic Chips Fabricated from Poly(methyl methacrylate) for the Detection of Low-Abundant DNA Mutations *Anal. Chem.* 2003, 75, 1130-1140.

[6] Noerholm, M.; Bruus, H.; Jakobseh, M. H.; Telleman, P.; Ramsing, N. B; Polymer microfluidic chip for online monitoring of microarray hybridizations, *Labchip,* 2004, 4, 28-37.

[7] Anderson, R. C.; Su, X.; Bogdan, G. J.; Fenton, J. A miniature integrated device for automated multistep genetic assays. *Nucl. Acids Res.* 2000, 28, e60.

[8] Lee, H. J.; Goodrich, T. T.; Corn, R. M. SPR imaging measurements of 1-D and 2-D DNA microarrays created from microfluidic channels on gold thin films. *Anal. Chem.* 2001, 73, 5525-5531.

[9] Liu, R. H.; Chen, H.; Luehrsen, K. R.; Ganser, D.; Weston, D.; Blackwell, J.; Grodzinski, P. Highly parallel integrated microfluidic biochannel arrays. Micro Electro Mechanical Systems, 2001. The 14th IEEE International Conference, 2001, 439-442.

[10] Hirschberg, D.; Jagerbrink, T.; Samskog, J.; Gustafsson, M.; Stahlberg, M.; Alvelius, G.; Husman, B.; Carlquist, M.; Jornvall, H.; Bergman, T.; Detection of Phosphorylated Peptides in Proteomic Analyses Using Microfluidic Compact Disk Technology. *Anal. Chem.* 2004, 76, 5864-5871.

[11] Dodge, A.; Turcatti, G.; Lawrence, I.; de Rooij, N. F.; Verpoorte, E. A microfluidic platform using molecular beacon-based temperature calibration for thermal hybridization of surface-bound DNA. *Anal. Chem.* 2004, 76, 1778-1787.

[12] Situma, C; Wang, Y.; Hupert, M.; Barany, F. McCarley, R. L.; Soper, S. A. Fabrication of DNA Microarrays one poly (methylmethacrylate) with ultraviolet patterning and microfluidics for the detection of low-abundant point mutations. Anal Biochem. 2005, 340, 123-135.

[13] Oehman, O. "Circular disk containing microchannel/microcavity structures", U.S. Pat. No. 6,620,478, 2003.

[14] Gustafsson, M.; Hirschberg, D.; Palmberg, C; Jörnvall, H.; Bergman; T. "Integrated Sample Preparation and MALDI Mass Spectrometry on a Microfluidic Compact Disk, Anal. Chem. 2004, 76, 345-350.

[15] Virtanen, J. "Optical disk-based assay devices and methods", U.S. Pat. No. 6,342,349, 2002.

[16] "Devices and methods for using centripetal acceleration to drive fluid movement in a microfluidics system", U.S. Pat. No. 6,709,869.

[17] Duffy, David C; Gillis, Heather L.; Lin, Joe; Sheppard, Norman F.; Jr.; Kellogg, Gregory J. Microfabricated Centrifugal Microfluidic Systems: Characterization and Multiple Enzymatic Assays. Anal. Chem., 1999, 71 (20), 4669-4678.

[18] Kellogg, G. J.; Arnold, T. E.; Carvalho, B. L.; Duffy, D. C.; Sheppard, N. F. "Centrifugal microfluidics: Applications", in Proc. Micro Total Analysis Systems 2000, Van den Berg, A; Olthuis, W.; Bergveld, E. eds. pp 239-142.

[19] Lai, S.; Wang, S.; Luo, J.; Lee, L. J.; Yang, S. T.; Madou, M. J. "Design of a Compact Disk-like Microfluidic Platform for Enzyme-Linked Immunosorbent Assay" Anal. Chem. 2004, 76, 1832-1837.

[20] Zoval, J. V.; Madou, M. J. Centrifuge-based fluidic platforms, *Proc. IEEE,* 2004, 92, 140-153.

[21] Madou, M. J.; Lee, L. J.; Daunert, S.; Lai, S. Y.; Shih. C. H.; Design and Fabrication of CD-like Microfluidic Platforms for Diagnostics: Microfluidic Functions. *Biomed. Microdevices* 2001, 3(3), 245-254.

[22] Jia, G. Ma, K. Zoval, J. V. and Madou, M. J. CD-based DNA Hybridization and Detection CD (compact disc)-based DNA Hybridization and Detection. Proceedings of SPIE International Symposium-Photonics Europe, Apr. 26-30, 2004, Strasbourg, France.

[23] Jean Philippe Stephan, Silvia Schanz, Anne Wong, Peter Schowl and Wai Lee T. Wong, "Development of a Frozen Cell Array as a High-Throughput Approach for Cell-Based Analysis," *American Journal of Pathology.* 2002; 161:787-797.

[24] Heejae Kim, Junsang Doh, Darrell J. Irvine, Robert E. Cohen and Paula T. Hammond, "Large Area Two-Dimensional B Cell Arrays for Sensing and Cell-Sorting Applications," Biomacromolecules 2004, 5, 822-82.

[25] Khademhosseini, A.; Suh, K. Y; Jon, S.; Eng. G; Yeh, J.; Chen, G.-J.; Langer, R.; A Soft Lithographic Approach To Fabricate Patterned Microfluidic Channels Anal. Chem., 2004, 7, 3675-3681.

[26] Chen, Christopher S.; Mrksich, Milan; Huang, Sui; Whitesides, George. M.; Ingber, Donald E. Micropatterned surfaces for control of cell, shape, position, and function. Biotechnology Progress 1998, 14(3), 356-363.

[27] Tokano, H.; Sul, J.; Mazzanti, M. L.; Doyle, R. T.; Haydon, P. G.; Porter, M. D. Micropatterned substrates: approach to probing intercellular communication pathways. Anal. Chem. 2002, 74, 4640-4646.

[28] Jiang, X.; Ng, J. M. K.; Stroock, A. D.; Dertinger, S. K. W.; Whitesides, G. M.; A Miniaturized, Parallel, Serially Diluted Immunoassay for Analyzing Multiple Antigens. J Am. Chem. Soc. 2003 125 5294-5295.

[29] Fukui S. et al. "Oligosaccharide microarrays for high-throughput detection and specificity assignments of carbohydrate-protein interactions", Nat. Biotech. 2002, 20, 1011-1017.

[30] Park S. et al, "Carbohydrate chips for studying high-throughput carbohydrate-protein interactions", J Am. Chem. Soc. 126, 2004, 4812-4819.

[31] Wang D. et al, "Carbohydrate microarrays for recognition of cross-reactive molecular markers of microbes and host cells", Nat. Biotech. 20, 2002, 275-281.

[32] Salisbury C. M.; et al "Peptide microarrays for the determination of protease substrate specificity," J Am. Chem. Soc. 124, 2002, 14868-14870.

[33] Uttamchandani M et al "Microarrays of tagged combinatorial trazine libraries in the discovery of small-molecule ligands of human IgG", J Comb. Chem. 6, 2004, 862-868.

[34] Uttamchandani M et al "Small molecule microarrays: recent advances and applications" Curr. Opin. Chem. Biol. 9, 2005, 4-13.

[35] Chen, X. et al. A Prototype Two-Dimensional Capillary Electrophoresis System Fabricated in Poly(dimethylsiloxane), Anal. Chem. 2002, 74, 1772-1778.

[36] C. J. Venkatramani et al. An Automated Orthogonal Two-Dimensional Liquid Chromatograph. Anal. Chem. 2003, 75, 3484-3494.

[37] David C. Wicks and Paul C. H. Li, "Separation of fluorescent derivatives of hydroxyl-containing small molecules on a microfluidic chip," Anal. Chim. Acta. 2004, 507, 107-114.

[38] Nagasawa K. et al. Transport Mechanism of antracycline derivatives in human leukemia cell lines: uptake and efflux of pirarubicin in H1 60 and pirarubicin-resistant HL 60 cells. Cancer Chemotherap. Pharmacol. 1996, 37, 297-304.

[39] Michael W. Sung and Paul C. H. Li, <<Chemical analysis of raw, dry-roasted and honey-roasted licorice by capillary electrophoresis,>> Electrophoresis, 2004, 25, 3434-3440.

[40] Paul C. H. Li, Guanghua Gao and Francis C. P. Law, "Validation of a capillary zone electrophoretic method for in vitro study of matrine transport through Caco-2 cells," J Liq. Chrom., 2004, 808, 209-214.

[41] S. Hu and Paul C. H. Li, "Conjugate formation between microcystin LR and protein phosphatase (PP2A) studied by capillary electrophoresis" Analyst, 2001, 126, 1001-1004.

[42] S. Hu and P. C. H. Li, "Micellar electrokinetic capillary chromatographic separation and fluorescent detection of amino acids derivatized with 7-fluoro-4-nitrobenzo-2-oxa-1,3-diazole" J. Chrom. A, 876, 2000, 183-191.

[43] S. Hu, E. Fu and P. C. H. Li, "Capillary electrophoretic separation enhanced by macrocyclic dioxopolyamine additive", J. Chrom. A., 844, 1999, 439-446. (Fu is a collaborator at Wuhan University.

[44] Paul C. H. Li, S. Hu, and P. K. S. Lam, "Development of a capillary electrophoretic method for the rapid separation and detection of hepatotoxic microcystins", Marine Pollution Bulletin, 39(1-12), 1999, 250-254.

[45] Duffy, D. C.; McDonald, J. C.; Schueller, O. J. A.; Whitesides, G. M. Rapid Prototyping of Microfluidic Systems in Poly(dimethylsiloxane). *Anal. Chem.,* 1998, 70 (23), 4974-4984.

[46] Wang, H.; Li, L.; Liu, H.; Liu, Q.; Mei, Q.; Wang, Y.; Zhu, J.; He, N.; Lu, Z. Label-free hybridization detection of a single nucleotide mismatch by immobilization of molecular beacons, on an agarose film. *Nucl. Acids. Res.* 2002, 30, e61, 1-9.

[47] Koch, C. A.; Paul C. H. Li and Utkhede R. S. "Identification of greenhouse pathogens by DNA hybridization on agarose coated glass slides", *Anal. Biochem.* 2005, 342, 93-102.

[48] Lenigk, R.; Liu. R. H.; Athavale, M.; Chen. Z. J.; Ganser, D.; Yang, J. N.; Rauch, C; Liu, Y. J.; Chan, B.; Yu, H. N.; Ray, M; Marrero, R.; Grodzinski, P Plastic biochannel hybridization devices: a new concept for microfluidic DNA arrays. *Anal. Biochem.* 2002, 311, 40-49.

[49] Erickson, D.; Li, D. Q.; Krull, U. J. Modelling of DNA hybridization kinetics for spatially resolved biochips. *Anal. Biochem.* 2003, 317, 186-200.

[50] Kuhdu, P. K.; Cohen I. M. Fluid Mechanics, $2^{nd}$ edition, Academic Press, San Diego, Calif., 2002.

[51] Carol Koch, Paul C. H. Li and Raj Utkhede, "Evaluation of thin films of agarose on glass for hybridization of DNA to identify plant pathogens with microarray technology", Anal. Biochem. 2005, 342, 93-102

[52] Koh, W. G. et al. Molding of Hydrogel Microstructures to Create Multiphenotype Cell Microarrays, Anal. Chem, 2003, 75, 5783-5789.

[53] Heo, J. et al. A Microfluidic Bioreactor Based on Hydrogel-Entrapped *E. coli*: Cell Viability, Lysis, and Intracellular Enzyme Reactions Anal. Chem. 2003, 75, 22-26.

[54] Chen, C. S. et al. Micropatterned surfaces for control of cell shape, position, and function. Biotech. Prog. 1998, 14(3), 356-363.

[55] Scudiero D A, et al. Evaluation of a soluble tetrazolium formazan assay for cell growth and drug sensitivity in culture using human and other tumor cell lines. Cancer Res. 1988, 48, 4827-4833.

[56] Larry Peng and Paul C. H. Li, "A three-dimensional flow control concept for single-cell experiments on a microchip (I): cell selection, cell retention, cell culture, cell balancing and cell scanning", Anal. Chem., 2004, 76, 5273-5281, and (II): Fluorescein diacetate metabolism and calcium mobilization in a single yeast cell as stimulated by glucose and pH changes", Anal. Chem. 2004, 76, 5282-5292.;

[57] Xiujun Li and Paul C. H. Li, "Microfluidic Selection and Retention of a Single Cardiac Myocyte, On-Chip Dye Loading, Cell contraction by Chemical Stimulation, and Quantitative Fluorescent Analysis of Intracellular Calcium" Anal. Chem., 2005, 77, 4315-4322.

[58] Paul C. H. Li, Laurent de Camprieu, Jia Cai and Monika Sangar, "Transport, retention and fluorescent measurement of single biological cells studied in microfluidic chips", LabChip, 2004, 4, 174-180.

[59] Nakshatri, H. et al. Constitutive activation of NF-kappaB during progression of breast cancer to hormone-independent growth. Mol. Cell. Biol. 1997, 17:3629-39.

[60] Sternson, S. M. et al, Split-Pool synthesis of 1,3-Dioxanes Leading to Arrayed stock solutions of single compounds sufficient for multiple phenotypic and protein-binding assays, JACS, 2001, 123, 1740-1747.

[61] Kuruvilla, F. G. et al, Dissecting glucose signaling with diversity-oriented synthesis and small-molecule microarrays. Nature, 2002, 416, 653-657.

[62] Lee, J. N. et al. Solvent Compatibility of PDMS-Based Microfluidic Devices. Anal. Chem. 2003, 75 6544-6554.

[63] Lahann, J. et al. Reactive Polymer Coatings: A First Step, toward Surface Engineering of Microfluidic Devices. Anal. Chem. 2003, 75, 2117-2122.

What is claimed is:

1. A microarray device comprising:
(a) a test chip comprising a plurality of discrete, spatially predetermined test positions, each of the test positions being located at the intersection between a first predetermined reagent pattern and a second predetermined reagent pattern, wherein one of said first and second predetermined reagent patterns is a radial pattern and the other of said first and second predetermined reagent patterns is a spiral pattern, wherein said spiral pattern is defined by a plurality of discrete, non-overlapping spiral reagent lines applied to said test chip, each of said spiral reagent lines having an inner first end located in a central portion of said chip and an outer second end located in a peripheral portion of said chip; and
(b) at least one first reagent immobilized on said test chip at said test positions.

2. The microarray device as defined in claim 1, wherein said at least one first reagent comprises a plurality of reagents each immobilized on said test chip at a corresponding one of said test positions.

3. The microarray device as defined in claim 1, comprising a first channel plate sealingly connectable to said test chip, wherein said first channel plate comprises a plurality of first microfluidic channels for distributing said at least one first reagent on said test chip in said first predetermined reagent pattern.

4. The microarray device as defined in 3, wherein each of said first microfluidic channels comprises a first end and a second end and wherein said at least one first reagent is flowable through said first microfluidic channels between said first and second ends when said first channel plate is sealingly connected to said test chip to thereby distribute said at least one first reagent to said test locations.

5. The microarray device as defined in claim 4, wherein said test chip has a centrosymmetrical geometric shape and wherein said first end of each of said first microfluidic channels is applied to a central portion of said test chip and said second end of each of said first microfluidic channels is applied to a peripheral portion of said test chip when said first channel plate and said first test chip are assembled together.

6. The microarray device as defined in claim 5, wherein said first end of each of said first microfluidic channels is in fluid communication with a first reservoir and said second end of each of said first microfluidic channels is in communication with a second reservoir, wherein said reservoirs are obliquely angled relative to a central axis passing through a center of said first channel plate and extending perpendicular to said first channel plate.

7. The microarray device as defined in claim 3, wherein said second channel plate is formed from a polymeric material.

8. The microarray device as defined in claim 3, wherein each of said microfluidic channels has a capacity between about 0.1 and 100 microlitres of fluid.

9. The microarray device as defined in claim 1, comprising at least one second channel plate sealingly connectable to said test chip, wherein said second channel plate comprises a plurality of second microfluidic channels for distributing at least one second reagent on said test chip in said second predetermined reagent pattern.

10. The microarray device as defined in 9, wherein each of said second microfluidic channels comprises a first end and a second end and wherein said at least one second reagent is flowable through said second microfluidic channels between said first and second ends when said second channel plate is sealingly connected to said test chip to thereby expose said at least one first reagent to said at least one second reagent at said test locations.

11. The microarray device as defined in claim 10, wherein said test chip has a centrosymmetrical geometric shape and wherein said first end of each of said second microfluidic channels is applied to a central portion of said test chip and said second end of each of said microfluidic channels is applied to a peripheral portion of said test chip when said second channel plate and said first test chip are assembled together.

12. The microarray device as defined in claim 11, wherein said first end of each of said second microfluidic channels is in fluid communication with a first reservoir and said second end of each of said first microfluidic channels is in communication with a second reservoir, wherein said reservoirs are obliquely angled relative to a central axis passing through a center of said second channel plate and extending perpendicular to said second channel plate.

13. The microarray device as defined in claim 9, wherein said at least one second reagent comprises a plurality of different test samples.

14. The microarray device as defined in claim 9, wherein said at least one second reagent is selected from the group consisting nucleic acids, oligonucleotides, proteins, peptides, peptide-nucleic acids, oligosaccharides, antigens, immunoglobulins, cells, organelles, cell fragments, small molecules and chimeric molecules.

15. The microarray device as defined in claim 9, wherein said second channel plate is formed from a polymeric material.

16. The microarray device as defined in claim 15, wherein said polymeric material is polydimethylsiloxane.

17. The microarray device as defined in claim 16, wherein said polymeric material is coated to prevent degradation upon exposure to organic solvents.

18. The microarray device as defined in claim 1, wherein said at least one first reagent is selected from the group consisting of nucleic acids, oligonucleotides, proteins, peptides, peptide-nucleic acids, oligosaccharides, antigens, immunoglobulins, cells, organelles, cell fragments, small molecules and chimeric molecules.

19. The microarray device as defined in claim 1, wherein said test chip has a centrosymmetrical geometric shape.

20. The microarray device as defined in claim 19, wherein said test chip is circular.

21. The microarray device as defined in claim 1, wherein said test chip is a coated glass substrate.

22. The microarray device as defined in claim 21, wherein said substrate is an aldehyde-functionalized glass substrate.

23. The microarray device as defined in claim 1, wherein said inner end of one of said spiral reagent lines is located at a position opposite said inner end of another one of said spiral reagent lines.

24. A microarray device comprising:
(a) a test chip comprising a plurality of discrete, spatially predetermined test positions, each of the test positions being located at the intersection between a first predetermined reagent pattern and a second predetermined reagent pattern; and
(b) at least one first reagent immobilized on said test chip at said test positions,
wherein one of said first and second predetermined reagent patterns is a right spiral pattern and the other of said first and second predetermined reagent patterns is a left spiral pattern.

25. A kit for forming a microfluidic microarray assembly (MMA) comprising:
(a) a test chip comprising a plurality of discrete, spatially predetermined test positions, wherein each of said test positions is located at the intersection between a first predetermined reagent pattern and a second predetermined reagent pattern, wherein one of said first and second predetermined reagent patterns is a radial pattern and the other of said first and second predetermined reagent patterns is a spiral pattern;
(b) a first channel plate sealingly connectable to said test chip, wherein said first channel plate comprises a plurality of first microfluidic channels for distributing at least one first reagent on said test chip in said first predetermined reagent pattern; and
(c) a second channel plate sealingly connectable to said test chip, wherein said second channel plate comprises a plurality of second microfluidic channels for distributing at least one second reagent on said test chip in said second predetermined reagent pattern.

26. The kit as defined in claim 25, wherein said first and second channel plates are sequentially connectable to said test chip to deliver said at least one first reagent and said at least one second reagent to said predetermined test positions.

27. The kit as defined in claim 25, further comprising a detector for detecting reactivity between said at least one first reagent and said at least one second reagent at said test positions.

28. The kit as defined in claim 25, wherein said at least one first reagent comprises a plurality of probes and wherein said at least one second reagent comprises a plurality of test samples.

29. The kit as defined in claim 25, wherein said at least one first reagent is selected from the group consisting of nucleic acids, oligonucleotides, proteins, peptides, peptide-nucleic acids, oligosaccharides, antigens, immunoglobulins, cells, organelles, cell fragments, small molecules and chimeric molecules.

30. The kit as defined in claim 25, wherein said at least one second reagent is selected from the group consisting of nucleic acids, oligonucleotides, proteins, peptides, peptide-nucleic acids, oligosaccharides, antigens, immunoglobulins, cells, organelles, cell fragments, small molecules and chimeric molecules.

31. The kit as defined in claim 25, wherein said test chip and said first and second channel plates each have a centrosymmetrical geometric shape.

32. The kit as defined in claim 31, wherein said shape is circular.

33. The kit as defined in claims 25, wherein said test chip is a coated glass substrate.

34. The kit as defined in claim 33, wherein said substrate is an aldehyde-functionalized glass substrate.

35. The kit as defined in claim 33, wherein said first channel plate and said second channel plates are formed from a polymeric material.

36. The kit as defined in claim 35, wherein said polymeric material is polydimethylsiloxane.

37. The kit as defined in claim 35, wherein said polymeric material is coated to prevent degradation upon exposure to organic solvents.

38. The kit as defined in claims 25, wherein each of said microfluidic channels has a capacity between about 0.1 and 100 microlitres of fluid.

39. A kit for forming a microfluidic microarray assembly (MMA) comprising:
(a) a test chip comprising a plurality of discrete, spatially predetermined test positions, wherein each of said test positions is located at the intersection between a first predetermined reagent pattern and a second predetermined reagent pattern;
(b) a first channel plate sealingly connectable to said test chip, wherein said first channel plate comprises a plurality of first microfluidic channels for distributing at least one first reagent on said test chip in said first predetermined reagent pattern; and
(c) a second channel plate sealingly connectable to said test chip, wherein said second channel plate comprises a plurality of second microfluidic channels for distributing at least one second reagent on said test chip in said second predetermined reagent pattern;
wherein one of said first and second predetermined reagent patterns is a right spiral pattern and the other of said first and second predetermined reagent patterns is a left spiral pattern.

40. A microfluidic microarray subassembly comprising:
(a) a test chip comprising a plurality of discrete, spatially predetermined test positions, wherein each of said test positions is located at the intersection between a first predetermined reagent pattern and a second predetermined reagent pattern, wherein one of said first and second predetermined reagent patterns is a radial pattern and the other of said first and second predetermined reagent patterns is a spiral pattern, and wherein at least one first reagent is immobilized on said test chip at said test positions; and
(b) a sample channel plate sealingly connectable to said test chip, wherein said channel plate comprises a plurality of microfluidic channels for distributing at least one second reagent on said test chip in said second predetermined reagent pattern.

41. A microarray device for determining reactivity between a plurality of probe reagents and a plurality of sample reagents, said microarray device comprising:
(a) centrosymmetrical test chip comprising a first array of said probe reagents arranged in a first predetermined pattern, wherein said probe reagents are immobilized on said chip at a plurality of discrete test positions; and
(b) a sample channel plate sealingly connectable to said test chip for applying said sample reagents thereto, wherein said sample channel plate comprises a plurality of microfluidic channels configured to apply said sample reagents to said test chip in a second array having a second predetermined pattern differing from said first predetermined pattern, wherein at least one of said first and second predetermined patterns is a radial pattern and the other of said first and second predetermined reagent patterns is a spiral pattern and wherein said first and second arrays intersect at said test positions when said sample plate is connected to said test chip and said sample reagents are flowed through said microfluidic channels.

42. A method of forming a microfluidic microarray assembly (MMA) comprising:
 (a) providing a test chip;
 (b) providing a first channel plate sealingly connectable to said test chip for applying at least one first reagent to said test chip, wherein said first channel plate comprises a plurality of first microfluidic channels configured in a first predetermined reagent pattern;
 (c) assembling said first channel plate to said test chip;
 (d) flowing said at least one first reagent through said first microfluidic channels to form a first array of said at least one first reagent on said test chip in said first predetermined reagent pattern;
 (e) immobilizing said at least one first reagent on said test chip at least some test locations of said first array;
 (f) removing said first channel plate from said test chip;
 (g) providing a second channel plate sealingly connectable to said test chip for applying at least one second reagent to said test chip, wherein said second channel plate comprises a plurality of second microfluidic channels configured in a second predetermined pattern differing from said first predetermined pattern,
 wherein one of said first and second predetermined reagent patterns is a radial pattern and the other of said first and second predetermined reagent patterns is a spiral pattern;
 (h) assembling said second channel plate to said test chip; and
 (i) flowing said at least one second reagent through said second microfluidic channels to form a second array of said at least one second reagent on said test chip in said second predetermined reagent pattern, wherein said second array intersects said first array at least said test locations.

43. The method as defined in claim 42, further comprising detecting any reactivity between said at least one first reagent and said at least one second reagent at said test locations.

44. The method as defined in claim 43, wherein said step of detecting any reactivity comprises detecting any hybridization products at said test locations.

45. The method as defined in claim 43, wherein said step of detecting any reactivity comprises detecting any reaction products at said test locations.

46. The method as defined in claim 43, wherein said step of detecting any reactivity comprises detecting any changes in cellular parameters at said test locations.

47. The method as defined in claim 43, wherein said step of detecting any reactivity is automated.

48. The method as defined in claim 42, wherein said at least one first reagent comprises a plurality of different probes, wherein each of said probes is flowable through separate ones of said first microfluidic channels.

49. The method as defined in claim 48, wherein said at least one second reagent comprises a plurality of different test samples, wherein each of said samples is flowable through separate ones of said second microfluidic channels.

50. The method as defined in claim 48, wherein said immobilizing comprises chemically bonding said probes to said test chip.

51. The method as defined in claim 48, wherein said immobilizing comprises adhering said probes to said test chip.

52. The method as defined in claim 49, wherein said probes and said test samples are each selected from the group consisting of nucleic acids, oligonucleotides, proteins, peptides, peptide-nucleic acids, oligosaccharides, antigens, immunoglobulins, cells, organelles, cell fragments, small molecules and chimeric molecules.

53. The method as defined in claim 42, wherein each of said first microfluidic channels comprises an inlet reservoir at one end thereof and an outlet reservoir at the other end thereof, and wherein said flowing said at least one first reagent through said first microfluidic channels comprises introducing a first fluid containing said at least one first reagent into said inlet reservoir and distributing said first fluid to said outlet reservoir.

54. The method as defined in claim 53, wherein said flowing of said at least one first reagent through said microfluidic channels comprises applying a force to said first channel plate.

55. The method as defined in claim 54, wherein said force is selected from the group consisting of centrifugal force, hydrodynamic force and electrokinetic force.

56. The method as defined in claim 55, wherein said test chip and first channel plate together form a centrosymmetrical first subassembly and wherein said force is a centrifugal force applied by spinning said first subassembly.

57. The method as defined in claim 56, wherein said centrosymmetrical first subassembly is circular.

58. The method as defined in claim 42, wherein each of said second microfluidic channels comprises an inlet reservoir at one end thereof and an outlet reservoir at the other end thereof, and wherein said flowing said at least one second reagent through said second microfluidic channels comprises introducing a second fluid containing said at least one second reagent into said inlet reservoir and distributing said second fluid to said outlet reservoir.

59. The method as defined in claim 58, wherein said flowing of said at least one second reagent through said microfluidic channels comprises applying a force to said second channel plate.

60. The method as defined in claim 59, wherein said force is selected from the group consisting of centrifugal force, hydrodynamic force and electrokinetic force.

61. The method as defined in claim 60, wherein said test chip and second channel plate together form a centrosymmetrical second subassembly and wherein said force is a centrifugal force applied by spinning said second subassembly.

62. The method as defined in claim 61, wherein said centrosymmetrical second subassembly is circular.

63. The method as defined in claim 42, further comprising coating said first or second microfluidic channels to enhance the organic solvent resistant properties thereof.

64. The method as defined in claim 42, wherein said at least one first reagent comprises cells and wherein said method comprises, prior to assembling said first channel plate to said test chip:
 (a) applying a first mask to said test chip to transfer a cell non-adherent material to said test chip, wherein said first mask comprises a plurality of first mask microfluidic channels configured in said second predetermined reagent pattern; and (b) introducing a cell-adherent solution into said first mask microfluidic channels to transfer said cell-adherent solution to said test chip in said second predetermined reagent pattern.

65. The method as defined in claim 64, comprising, after removing said first channel plate from said test chip:
(a) applying a second mask to said test chip to transfer a cell viability promoting material to said test chip, wherein said mask comprises a plurality of second mask microfluidic channels configured in said second predetermined reagent pattern; and
(b) introducing said cell viability promoting material into said second mask microfluidic channels in said second predetermined reagent pattern.

66. The method as defined in claim 65, wherein said cell-adherent solution comprises fibronectin and said cell viability promoting material comprises a hydrogel.

67. A method of forming a microfluidic microarray assembly (MMA) comprising:
(a) providing a test chip:,
(b) providing a first channel plate sealingly connectable to said test chip for applying at least one first reagent to said test chip, wherein said first channel plate comprises a plurality of first microfluidic channels configured in a first predetermined reagent pattern;
(c) assembling said first channel plate to said test chip;
(d) flowing said at least one first reagent through said first microfluidic channels to form a first array of said at least one first reagent on said test chip in said first predetermined reagent pattern;
(e) immobilizing said at least one first reagent on said test chip at least some test locations of said first array;
(f) removing said first channel plate from said test chip;
(g) providing a second channel plate sealingly connectable to said test chip for applying at least one second reagent to said test chip, wherein said second channel plate comprises a plurality of second microfluidic channels configured in a second predetermined reagent pattern differing from said first predetermined pattern;
(h) assembling said second channel plate to said test chip; and
(i) flowing said at least one second reagent through said second microfluidic channels to form a second array of said at least one second reagent on said test chip in said second predetermined reagent pattern, wherein said second array intersects said first array at least said test locations;
wherein one of said first and second predetermined reagent patterns is a right spiral pattern and the other of said first and second predetermined reagent patterns is a left spiral pattern.

68. A method of using a microarray subassembly produced by a method comprising: (1) providing a test chip; (2) providing a first channel plate sealingly connectable to said test chip for applying at least one first reagent to said test chip, wherein said first channel plate comprises a plurality of first microfluidic channels configured in a first predetermined pattern; (3) assembling said first channel plate to said test chip; (4) flowing said at least one first reagent through said first microfluidic channels to form a first array of said at least one first reagent on said test chip in said first predetermined pattern; (5) immobilizing said at least one first reagent on said test chip at least some test locations of said first array; and (f) removing said first channel plate from said test chip, the method of using said microarray subassembly comprising:
(a) providing a second channel plate sealingly connectable to said test chip for applying at least one second reagent to said test chip, wherein said second channel plate comprises a plurality of second microfluidic channels configured in a second predetermined pattern differing from said first predetermined pattern;
(b) assembling said second channel plate to said test chip;
(c) flowing said at least one second reagent through said second microfluidic channels to form a second array of said at least one second reagent on said test chip in said second predetermined pattern, wherein said second array intersects said first array at least said test locations; and
(d) detecting any reactivity between said first reagent and said second reagent at said test locations;
wherein one of said first and second predetermined reagent patterns is a radial pattern and the other of said first and second predetermined reagent patterns is a spiral pattern.

69. The method of claim 68, wherein said at least one second reagent is flowed through said second microfluidic channels by applying a centrifugal force to said second channel plate.

70. A method of distributing first and second reagents on a test chip comprising:
(a) providing a microfluidic microarray device, wherein said device comprises said test chip and first and second channel plates sealingly connectable to said test chip, each of said channel plates having a plurality of microfluidic channels, wherein said first channel plate comprises microfluidic channels configured in a first predetermined pattern and said second channel plate comprises microfluidic channels configured in a second predetermined pattern;
wherein one of said first and second predetermined patterns is a radial pattern and the other of said first and second predetermined patterns is a spiral pattern, and wherein said first and second predetermined patterns intersecting at a plurality of predetermined test positions on said test chip, said method comprising:
sealingly connecting said first channel plate to said test chip to form a first subassembly and rotating said first subassembly to distribute said first reagent in at least some of said microfluidic channels configured in said first predetermined pattern by centrifugal force; and thereafter;
removing said first channel plate from said test chip and sealingly connecting said second channel plate to said test chip to form a second subassembly;
rotating said second subassembly to distribute a said second reagent in at least some of said microfluidic channels configured in said second predetermined pattern by centrifugal force, thereby causing said first and second reagents to interact at least some of said test positions on said test chip.

71. The method as defined in claim 70, comprising applying an electrical field to at least one of said first subassembly and said second subassembly prior to rotating said respective first subassembly and said second subassembly.

72. The method as defined in claim 70, further comprising immobilizing said first reagent on said test chip prior to rotating said second subassembly to distribute said second reagent.

73. The method as defined in claim 70, comprising rotating said first subassembly or said second subassembly at variable speeds to cause said first reagent or said second reagent to flow within selected microfluidic channels depending upon the speed of rotation selected.

74. A microarray device comprising:
(a) a test chip comprising a plurality of discrete, spatially predetermined test positions, each of the test positions being located at the intersection between a first predetermined reagent pattern and a second predetermined reagent pattern, wherein one of said first and second predetermined reagent patterns is a radial pattern and the other of said first and second predetermined reagent patterns is a spiral pattern; and
(b) a fluid distribution system for delivering reagent to said test chip in said first and second predetermined patterns, wherein said fluid distribution system comprises first and second channel plates which are sequentially connectable to said test chip, wherein each of said channel plates comprises microfluidic channels configured to deliver said reagent to said test chip in one of said patterns.

75. The device as defined in claim 74, wherein test chip is a compact disc.

76. The device as defined in claim 75, wherein said compact disc is circular.

77. The device as defined in claim 74, wherein said predetermined test positions are arranged in a non-rectangular microarray.

78. The device as defined in claim 77, wherein said microarray comprises greater than 256 test positions.

79. The device as defined in claim 78, wherein said microarray comprises greater than 400 test positions.

80. The device as defined in claim 77, wherein said microarray covers substantially all of the surface area of said test chip between a central portion thereof and a peripheral portion thereof.

81. The device as defined in claim 74, wherein said fluid distribution system comprises at least one reservoir on at least one of said channel plates for receiving said reagent, wherein said reagent is delivered from said at least one reservoir through said microfluidic channels to said test positions on said test chip by the application of centrifugal force when said test chip is rotated with said at least one of said channel plates.

82. A method of distributing a reagent to a non-rectangular array of spatially predetermined test positions located on a test chip comprising:
(a) providing a centrosymmetrical test chip;
(b) providing a first channel plate having a plurality of micro fluidic channels configured in a first predetermined pattern;
(c) sealingly connecting said first channel plate and said test chip to form a first microfluidic microarray assembly (MMA) device;
(d) loading a test fluid comprising said reagent onto said first MMA device at a loading location in fluid communication with at least one of said channels;
(e) rotating said first MMA device to cause said test fluid to flow by centrifugal force from said loading location to said test positions;
(f) providing a second channel plate having a plurality of microfluidic channels configured in a second predetermined pattern;
(g) sealingly connecting said second channel plate and said test chip to form a second microfluidic microarray assembly (MMA) device;
(h) loading a test fluid comprising said reagent onto said first MMA device at a loading location in fluid communication with at least one of said channels; and
(i) rotating said second MMA device to cause said test fluid to flow by centrifugal force from said loading location to said test positions;
wherein one of said first and second predetermined reagent patterns is a radial pattern and the other of said first and second predetermined reagent patterns is a spiral pattern.

83. The method as defined in claim 82, further comprising generating detection data by detecting the presence of said reagent at said test positions.

84. The method as defined in claim 82, comprising transforming said detection data from a non-rectangular array format to a rectangular array format.

* * * * *